United States Patent
Brennan

(10) Patent No.: US 9,259,246 B2
(45) Date of Patent: Feb. 16, 2016

(54) SPINAL STABILIZATION SYSTEM AND METHOD

(76) Inventor: William A. Brennan, Lafayette, LA (US)

(*) Notice: Subject to any disclaimer, the term of this patent is extended or adjusted under 35 U.S.C. 154(b) by 528 days.

(21) Appl. No.: 13/571,412

(22) Filed: Aug. 10, 2012

(65) Prior Publication Data
US 2014/0046445 A1 Feb. 13, 2014

(51) Int. Cl.
| | | |
|---|---|---|
| *A61B 17/70* | (2006.01) | |
| *A61B 17/86* | (2006.01) | |
| *A61F 2/44* | (2006.01) | |
| *A61F 2/28* | (2006.01) | |
| *A61F 2/46* | (2006.01) | |
| *A61F 2/30* | (2006.01) | |

(52) U.S. Cl.
CPC .......... *A61B 17/7032* (2013.01); *A61B 17/7034* (2013.01); *A61B 17/7044* (2013.01); *A61B 17/7059* (2013.01); *A61B 17/8685* (2013.01); *A61F 2/4455* (2013.01); *A61F 2002/2835* (2013.01); *A61F 2002/30062* (2013.01); *A61F 2002/30677* (2013.01); *A61F 2002/4677* (2013.01); *A61F 2310/00017* (2013.01); *A61F 2310/00023* (2013.01); *A61F 2310/00029* (2013.01)

(58) Field of Classification Search
CPC ........................... A61F 2/4455; A61B 17/7044
See application file for complete search history.

(56) References Cited

U.S. PATENT DOCUMENTS

| | | | |
|---|---|---|---|
| 5,520,690 | A | 5/1996 | Errico |
| 5,562,735 | A | 10/1996 | Margulies et al. |
| 6,613,051 | B1 | 9/2003 | Luk et al. |
| 8,936,626 | B1 * | 1/2015 | Tohmeh et al. ............... 606/279 |
| 2004/0177847 | A1 | 9/2004 | Foley et al. |
| 2005/0027359 | A1 * | 2/2005 | Mashburn .................. 623/17.11 |
| 2009/0204155 | A1 | 8/2009 | Aschmann |
| 2010/0010494 | A1 | 1/2010 | Quirno |
| 2010/0076502 | A1 | 3/2010 | Guyer et al. |
| 2010/0268234 | A1 | 10/2010 | Aho et al. |

FOREIGN PATENT DOCUMENTS

WO          2012106013          8/2012

OTHER PUBLICATIONS

Arman et al., "The human sacrum and safe approaches for screw placement", Journal of Clinical Neuroscience (2009) 16: 1046-1049.
International Search Report and Written Opinion mailed on Nov. 7, 2013 in PCT Application No. PCT/US13/54369. (15 pages).
Neumann et al., "Determination of inter-spinous process distance in the lumbar spine. Evaluation of reference population to facilitate detection of severe trauma", Eur Spine J (1999) 8(4): 272-278.
Nirvan et al., "A study of inter-pedicular distances of the lumbar vertebrae measured in plain antero-posterior radiograph in Gujaratis", J Anat Soc India (2005) 54(2): 1-9.

* cited by examiner

*Primary Examiner* — Nicholas Woodall
(74) *Attorney, Agent, or Firm* — Novak Druce Connolly Bove + Quigg LLP.

(57) ABSTRACT

A method for stabilizing the spine at the level of one or more vertebrae includes the step of inserting a pedicle connector through the pedicle of a vertebra from one of the anterior side and posterior side of the vertebra to the other of the anterior side and the posterior side of the vertebra. The pedicle connector is secured to a stabilization construct positioned adjacent to either the anterior side or posterior side of the vertebra. The process is repeated for the opposite side of the pedicle connector. A system for stabilizing the spine and a pedicle connector are also disclosed.

4 Claims, 36 Drawing Sheets

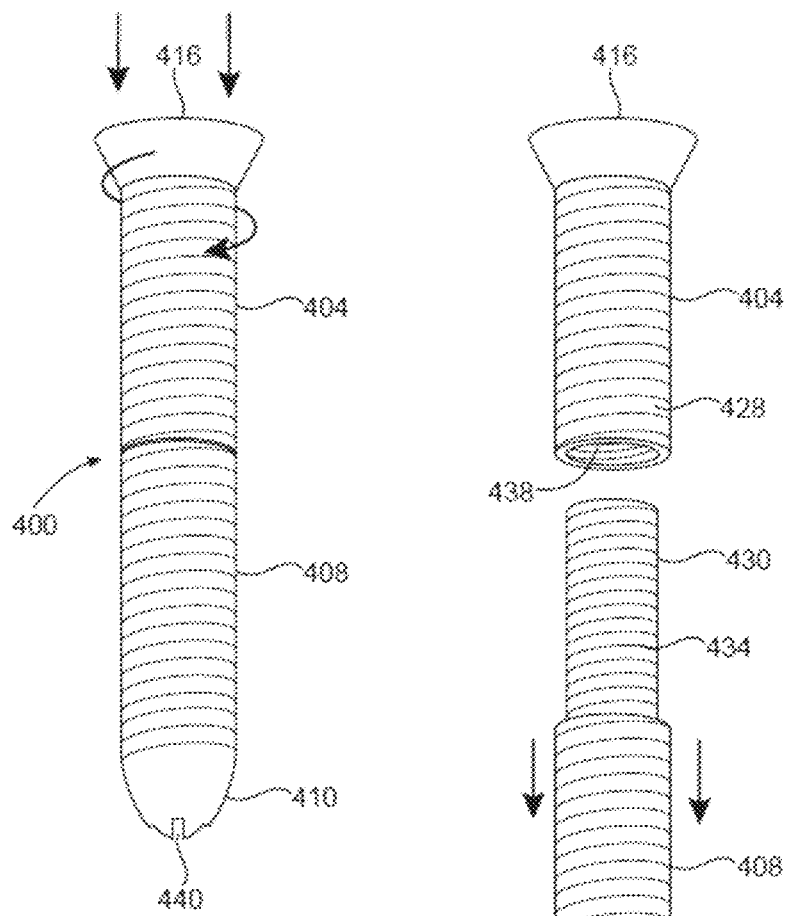
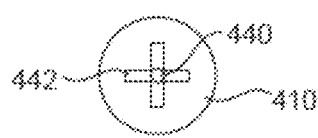
FIG. 36A
FIG. 36B
FIG. 36C

SPINAL STABILIZATION SYSTEM AND METHOD

FIELD OF THE INVENTION

This invention relates generally to spinal implant devices, and more particularly to spinal stabilization systems and methods

BACKGROUND OF THE INVENTION

The human spine is comprised of bony vertebrae separated by softer discs and has been the subject of surgical interest for several decades. Since the 1950s spine surgeons have used metallic hardware to increase the success of stabilization surgery. Many spinal disorders lead to spinal instability and surgeons have used the process of bone healing to fuse spinal segments using bone grafts from either the patient or other sources. The addition of spinal hardware in spine surgery has significantly increased the success rate from these bone healing operations commonly known as fusion operations. Spinal hardware or instrumentation has been a developing field of spine surgery and has involved merging the hardware with various portions of the human vertebra.

The human vertebras are commonly divided into four major regions with a corresponding numbering system. The cervical spine has seven vertebra, the thoracic spine has twelve, and the lumbar spine has five. The sacrum, or tailbone as it is commonly referred to, is considered one mechanical bone segment but is actually made up of many fused segments during human gestation. The human vertebral diagram (FIGS. 1-2) shows the basic vertebral features, the vertebra 40 includes a vertebral body (41), the pedicle (42), the transverse process (43), the facet joint (44), the lamina (45), and the spinous process (46). All of these features can be found on vertebra in the cervical, thoracic and lumbar spine.

In the 1970's advances were made in spine instrumentation by the development of screw stabilization systems that utilized the pedicle of the vertebra for anchoring of the screws. Surgeons would use these systems by passing screws from the posterior approach into the vertebral body. These systems were commonly used as paired pedicle screw systems and the increased stabilization strength led to fewer complications from fusion failure. More recently stabilization systems utilizing the anterior approach to the spine have been developed and have used various screw stabilization technologies. The anterior stabilization systems utilize screw stabilization frequently to hold anterior spinal hardware in place. The anterior screw stabilization systems previously described get most of their holding power from the cortical bone in the anterior and lateral portion of the vertebral body. One of the most devastating complications from spinal stabilization implantation is the phenomena of hardware "pullout". This term refers to when the mechanism relied upon to hold either anterior or posterior stabilization hardware fails to hold the hardware in place and the hardware becomes dislodged. With anterior hardware the failure results in the hardware lifting off of the spine as the screw fixation pulls through the cortical bone of the vertebral body. In posterior hardware cases, the pedicle screws pull out of the pedicle and the hardware attached posteriorly becomes dislodged pulling away from the spine posteriorly. In either instance, the stabilization mechanism whether it be screws in the anterior area or hooks or screws in the posterior area fail to provide the stability for which they were intended and reoperation becomes more likely usually involving extension of the stabilization to involve even more levels of the spine. Often the areas of attachment where the pullout occurred are no longer usable for a stabilization point because of the damaged bone texture in that area. Technology that reduces this pullout phenomenon is needed to reduce the hardware failure rate and subsequent fusion failure and reoperation rate.

As intraoperative imaging technology and endoscopic techniques have advanced, so too has the ability of the surgeon to form a more precise relationship when using spine instrumentation and the tools with which it is inserted. Over the years these have advanced from customary anatomical landmarks combined with the eye of the surgeon through the development of intraoperative radiographs, fluoroscopic techniques, and more recently intraoperative volumetric computer-assisted navigational technology and endoscopic technology. As these imaging technologies have advanced, accordingly, spinal instrumentation must advance in terms of the accuracy of hardware placement previously considered only possible with large incisions and increased surgical complication risk.

In addition to hardware pullout problems in healthy patients, one of the most challenging medical conditions facing spine surgeons is the patient with spinal instability as well as osteoporosis. Osteoporosis is a medical condition which lowers bone density and makes screw stabilization less successful by reducing the strength with which the screw holds into the bone substance. Screw pullout and hardware failure are significantly more common in patients with osteoporosis. Up to this point spinal stabilization systems for patients with osteoporosis have relied on supplementing the screw stabilization with special manufacturing processes on the surface of the screw to allow faster integration of the screw into the vertebra during bone healing. Other supplementary procedures have involved the introduction of cement into screw holes in osteoporotic patients to increase the strength of the screw relationship with the bone.

SUMMARY OF THE INVENTION

A method for stabilizing the spine at the level of one or more vertebra having anterior and posterior sides, comprises the steps of inserting a pedicle connector through the pedicle of the vertebra from one of the anterior side or posterior side of the vertebra to the other of the anterior side or posterior side of the vertebra; securing the pedicle connector to a stabilization construct positioned adjacent to either the anterior side of the pedicle connector or the posterior side of the pedicle connector, repeating the process for the opposite side of the pedicle connector.

The step of inserting pedicle connectors can comprise the step of positioning a guide wire through the vertebra to guide the placement of the connectors. A needle can be positioned through the vertebra, and the guide wire is directed through the needle and through the vertebra, and the needle is removed to leave the guide wire in position through the vertebra. The anterior stabilization construct can be threaded onto the wire(s) to position the stabilization construct adjacent to the anterior surface of the vertebra. The pedicle connector can be guided by the wire and positioned through the pedicle of the vertebra. The pedicle connector can be secured to the anterior stabilization construct by cooperating threaded portions on the pedicle connector and the stabilization construct, in one aspect by locking screws.

A stabilization construct can be placed over the wires on the posterior side of the vertebra and attached to the pedicle connectors. The pedicle connectors can be screws. The stabilization construct can be at least one selected from the group consisting of spinal hardware and a spinal anchor. The spinal hardware can be at least one selected from the group consisting of a rod, plate, connector, variable angle connector, corpectomy cage, an artificial disc, and interbody devices. The spinal anchor can provide at least a 10% increase over the outside diameter of the pedicle connector. The method can include performing a discectomy and inserting an interbody device. The anterior stabilization construct can involve anchoring only one vertebra or extend across two or more vertebral segments.

A system for stabilizing the spine can include an anterior stabilization construct; a pedicle connector for extending through the pedicle of a vertebra; engagement structure for securing the pedicle connector to the anterior stabilization construct; a posterior stabilization construct for attaching to the pedicle connector on a posterior side of the vertebra; and engagement structure for securing the posterior stabilization construct to the pedicle connector on the posterior side of the vertebra. The stabilization construct can be at least one selected from the group consisting of spinal hardware and a spinal anchor. The spinal hardware can comprise at least one selected from the group consisting of a rod, plate, connector, variable angle connector, corpectomy cage, an artificial disc, and interbody devices. The spinal anchor can provide at least a 10% increase over the outside diameter of the pedicle connector.

The pedicle connector can be composed of two parts which can be threaded together for insertion and each part may be removed from anterior or posterior approach respectively. The connector can comprise anterior parts and posterior parts, the anterior part and posterior part being detachably engagable.

A pedicle connector includes an anterior part and a posterior part. The anterior part and posterior part comprise engagement structure for detachably securing the anterior part to the posterior part. The anterior part and posterior part have bone threads for engaging bone as the screw is advanced through bone. The pedicle connector anterior and posterior parts may also be fitted together using alternate engaging means such as locking fasteners which allow independent anterior or posterior disengagement. The pedicle connector may also have an anterior part and posterior part that are not detachable nor disengageable.

The anterior part and posterior part have external cylindrical surfaces the external surfaces of the anterior part and the posterior part aligning when the anterior part is engaged to the posterior part. The engagement structure can comprise cooperating male and female threaded portions. The male threaded portion can be provided on a male protrusion on one of the anterior part or the posterior part, with a diameter less than the diameter of the external surface, and the female threaded portion can be provided on the other of the anterior part and the posterior part. Alternate external versions of the anterior and posterior parts of the pedicle connector may be oval, diamond shaped, square or other compatible geometries for placing through the pedicle.

BRIEF DESCRIPTION OF THE DRAWINGS

There are shown in the drawings embodiments that are presently preferred it being understood that the invention is not limited to the arrangements and instrumentalities shown, wherein:

FIG. 36 (A-C) is a detailed schematic side view of an A) assembled (threaded), B) end view, and C) unassembled (unthreaded) pedicle connector to be used with this stabilization system including the recessed cross fitting at the tip of the screw.

DETAILED DESCRIPTION OF THE INVENTION

Figure 1:
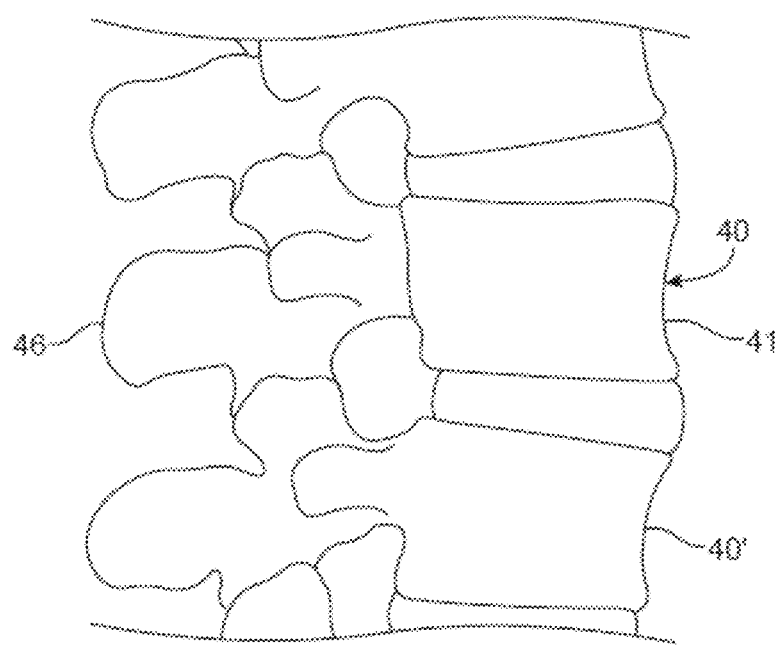
FIG. 1 is a side elevation of a spine.

This invention introduces an approach of combining anterior and posterior spinal stabilization or other treatment systems to produce a mechanically linked construct more resistant to failure in the setting of osteoporosis or other medical conditions where fusion or hardware failure is a concern. A pedicle connector is placed through one or more pedicles of one or more vertebrae at one or more levels. The anterior end of the pedicle connector extends anterior to the posterior cortex of the vertebral body. The posterior end of the pedicle connector extends to a position posterior to or at the level of the transverse process of the vertebral body. The pedicle connector can be placed either in an anterior-to-posterior direction or a posterior-to-anterior direction. A posterior spinal construct is attached to a posterior end of the pedicle connector, and an anterior spinal construct is attached to the anterior end of the pedicle connector. In an alternate embodiment, only one pedicle connector may be used at each vertebral level or in another embodiment paired pedicle connectors at one level and a single pedicle connector at another level may be used and any combination thereof.

The pedicle connector is elongated and can be with or without threads. The pedicle connector can be a screw. The pedicle connector can be a shaft. The pedicle connector can be threaded at the end that is guided through the pedicle of a vertebra, so as to engage the sides of the vertebral opening that is created by the surgeon for the insertion of the pedicle connector. Rotation of the pedicle connector will then thread the connector through the opening. The anterior and posterior ends of the pedicle connector have structure for attaching the pedicle connector to respective anterior and posterior spinal constructs. The anterior and posterior spinal constructs can have structure to engage ends of the pedicle connector, with or without cooperating engagement structure on the pedicle connector. This structure can be male or female threads. The pedicle connector can be a shaft and the anterior or posterior spinal constructs can engage the shaft with suitable structure such as set screws. Other attachment structure such as expansion screws is possible. The diameter of the pedicle connector can be between about 3 mm and about 10 mm. The anterior or posterior spinal construct can be spinal hardware or a spinal anchor. Different types of anterior and posterior spinal constructs can be attached to the ends of the pedicle connector. The anterior spinal construct can be any spinal construct attached to the vertebral body anterior to the posterior cortex of the vertebral body. The posterior spinal construct can be any spinal construct that attaches to the pedicle connectors posterior to or at the level of the transverse process of the vertebral body. The anterior and posterior spinal constructs are attached to the pedicle connectors and can serve as an anchor or fixation device for the connectors. The anterior and posterior spinal constructs can be a single device, or multiple devices which are connected or otherwise operate in concert to produce a desired effect on the spine. The anterior or posterior spinal constructs can function at one spinal level or span one or more vertebral segments above or below the pedicle connector spinal level. In one aspect a spinal anchor is attached to the pedicle connector at one of the anterior or posterior ends of the pedicle connector, and spinal hardware is attached to the other end of the pedicle connector.

Spinal hardware can be any device or material attached to any part of the spine for purposes of stabilizing spinal movement by either spanning across an intervertebral disc space or serving as an anchor for a spinal construct or otherwise is used for spinal stabilization. Spinal stabilization is the act of applying device(s) to the human spine that modify the movement of the spine, where modification can include restriction. Examples of spinal hardware include rods, plates (one body or multiple body attachments), connectors to connect the pedicle connector to other devices such as rods or plates, a variable angle connector which connects a pedicle connector to posterior rods or plates, a corpectomy cage, an interbody spacing device, an interbody cage, an artificial disc, and interbody devices. Commercially available examples include, but are not limited to, pedicle screw systems (TSRH, Legacy), anterior cervical discectomy and fusion plates (Atlantis), LT cages (Medtronic Inc. Minneapolis, Minn.), and V-Lift cage (Stryker Corporation. Kalamazoo, Mich.).

In one embodiment the spinal hardware is a stabilization cap. The stabilization cap has structure for engaging the pedicle connector and structure for engaging at least one other piece of spinal hardware. The stabilization cap thereby serves as a connector, connecting the pedicle connector to at least one other piece of spinal hardware. The stabilization cap can also serve to anchor or fix the pedicle screw in position in the vertebrae. The stabilization cap in one aspect permits a variety of different devices to be attached to the pedicle connector, such as rods, hooks, plates, variable angle connectors, with a common attachment scheme, such that the surgeon is provided with flexibility in the device type or size which is implanted into the patient, and such that these devices can be interchanged during an operation or during a subsequent operation without removal of the pedicle connector.

A spinal anchor can be any device attached to the anterior or posterior end of a pedicle connector that results in providing resistance to pull out phenomena in the opposite direction. In one aspect, the spinal anchor provides at least a 10% increase in outside diameter width as compared to the largest diameter of the pedicle connector. It may alternatively provide at least a 20% increase over the outside diameter of the pedicle connector. It may alternatively provide at least a 30% increase over the outside diameter of the pedicle connector.

The attachment of the anterior and posterior spinal constructs to the pedicle connectors may be either through a matching machine thread portion of the pedicle connectors near the posterior or anterior end of the connector or an alternate attachment may exist whereby the construct interlocks with the pedicle connector without threads. The anterior and posterior spinal constructs can be placed using minimally invasive techniques such as percutaneous placement or the construct (s) may be placed using standard open surgical techniques.

The anterior or posterior spinal construct and pedicle connectors can be flexible or rigid, and can be made of any suitable material including metals or plastics. The anterior and posterior spinal construct and pedicle connectors can be made of absorbable or non-absorbable materials as well as synthetic or drug eluting materials or any combination thereof. In the preferred embodiment a medical grade metallic material is used. In another embodiment a non-metallic material may be used. In another embodiment the spinal constructs and or pedicle connectors can be made of bone or bone-like material.

The anterior or posterior spinal construct may either have none or part of its components inside the disc space. Such spinal constructs incorporating the disc may be made of metal, bone or non-metal materials. The spinal construct could be attached to the surface of the vertebral body or the lateral aspect of the vertebral body. The construct could exist at only one vertebral body or span one or more disc spaces. The construct may be lateral at some levels, anterolateral at other levels and anterior at other levels. The spinal construct can be a plate. The plate can have a smooth surface or non-smooth. The anterior spinal construct may or may not have projections from the vertebral side of the construct that embed into the bone to prevent movement of the plate.

In the one embodiment, an anterior spinal construct is attached to a pedicle connector from the anterior approach as opposed to the more traditional posterior approach. The pedicle connectors go through the pedicle and emerge posteriorly. The patient is then closed up in front and turned over and a posterior spinal construct is attached to the connector. In one embodiment this posterior spinal construct is spinal hardware such as a rod.

A guide wire may be used on the anterior pedicle connector insertion and the guide wire would then project through the posterior musculature and subcutaneous tissue just under the skin. The patient would then be turned over after the anterior stabilization had been applied and the posterior portion of the procedure would begin with localizing the already placed guide wire with fluoroscopy and after making an appropriate skin incision, passing the threaded head of the stabilization cap over the guide wire and onto the tip of the pedicle connector. After the caps are in place, percutaneous passage of a connecting rod between the ipsilateral stabilization caps occurs followed by set screw tightening of the caps locking them to the connecting rod. Alternate embodiments using open surgical techniques are also possible with or without guide wires. The anterior spinal approach may be performed using either open laparotomy techniques or minimally invasive endoscopic techniques.

Figure 2:
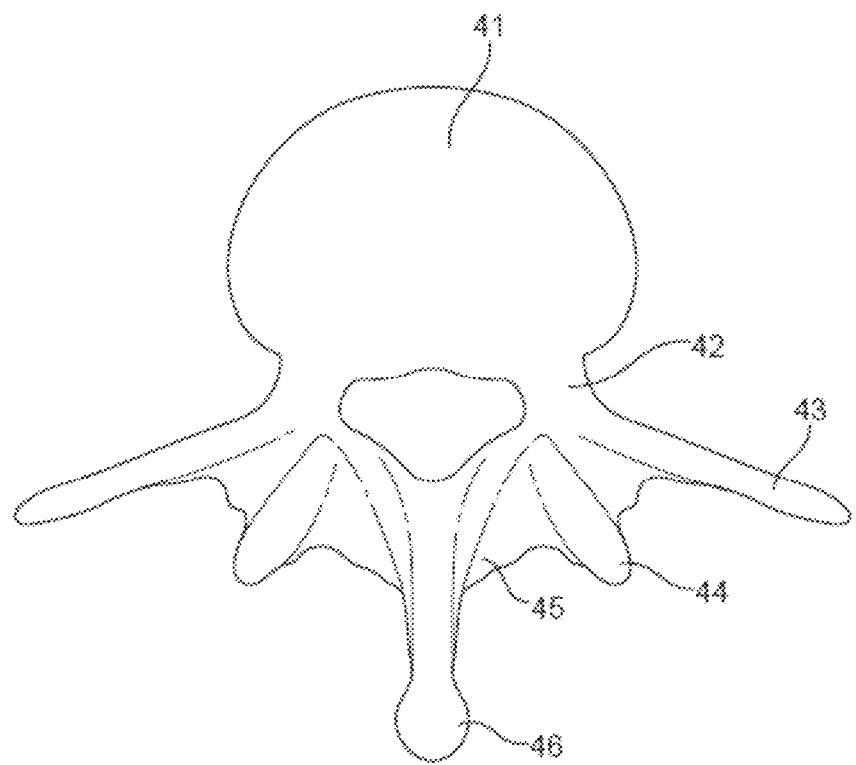
FIG. 2 is a plan view of a vertebra.

The patient's spinal level is selected. The invention is usable for all human spine work—cervical, thoracic and lumbar. In FIGS. 1-2 the lumbar system with a vertebra 40 is shown for purposes of illustration. FIGS. 1-2 show the basic vertebral features, the superior vertebra having vertebral body 41, the pedicle 42, the transverse process 43, the facet joint 44, the lamina 45, and the spinous process 46. Also shown is an inferior vertebra 40'. Once the segment(s) of the spine have been selected for the procedure, the spine is approached in cervical, thoracic, lumbar, or sacral regions using standard anterior exposure techniques.

Figure 3:
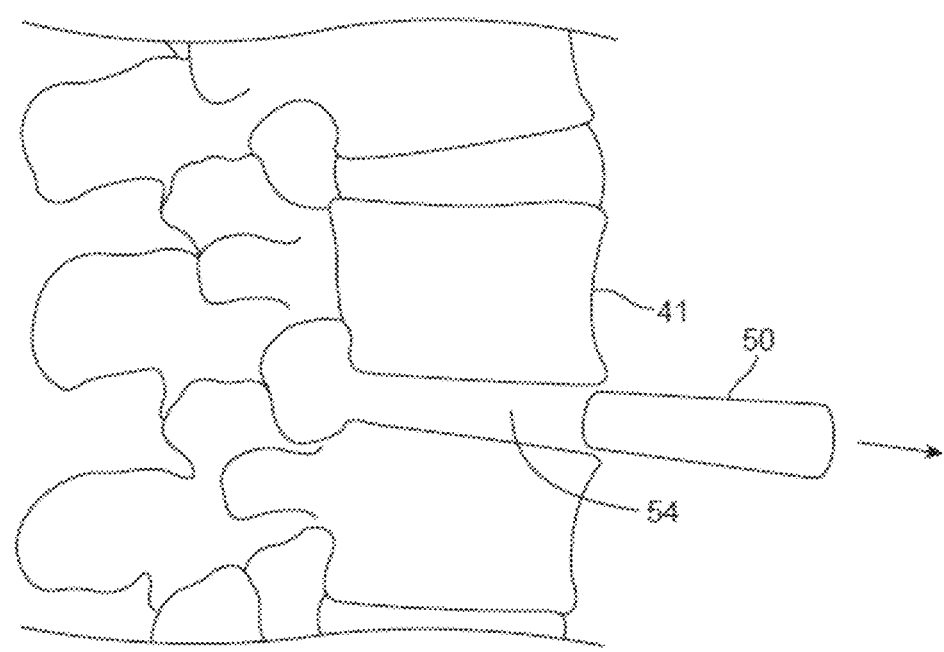
FIG. 3 is a schematic illustration of a discectomy.

FIG. 3 is a schematic illustration of a discectomy. The disc 50 and surrounding material is removed from the intervertebral space 54 in an anterior discectomy procedure.

Figure 4:
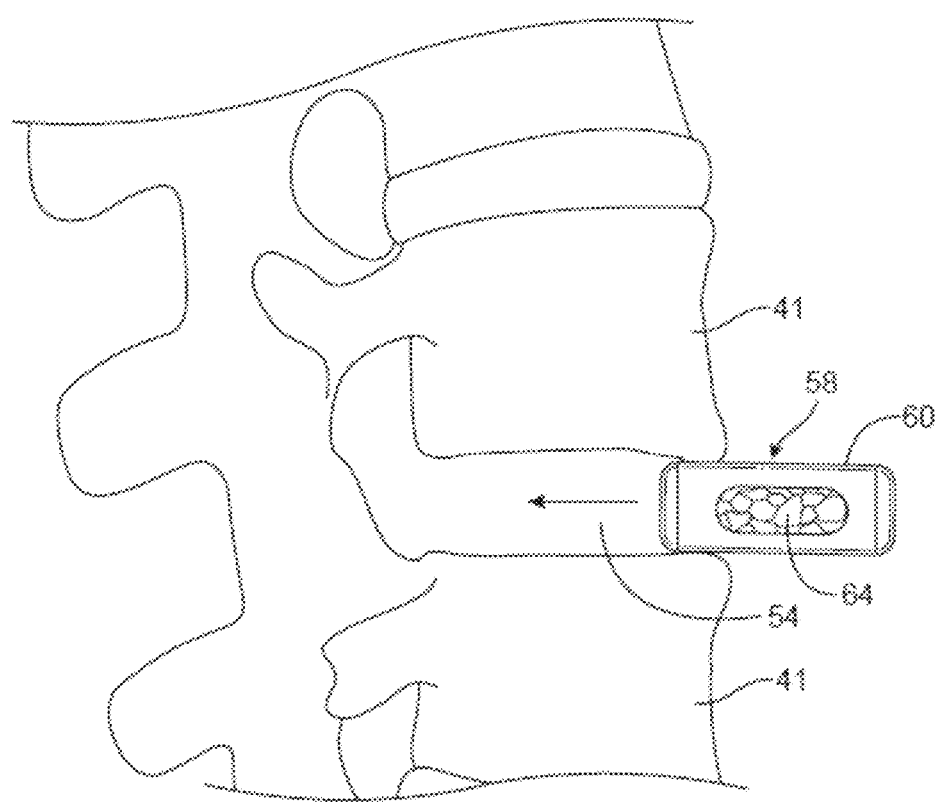
FIG. 4 is a schematic illustration of the insertion of an interbody device.
Figure 5:
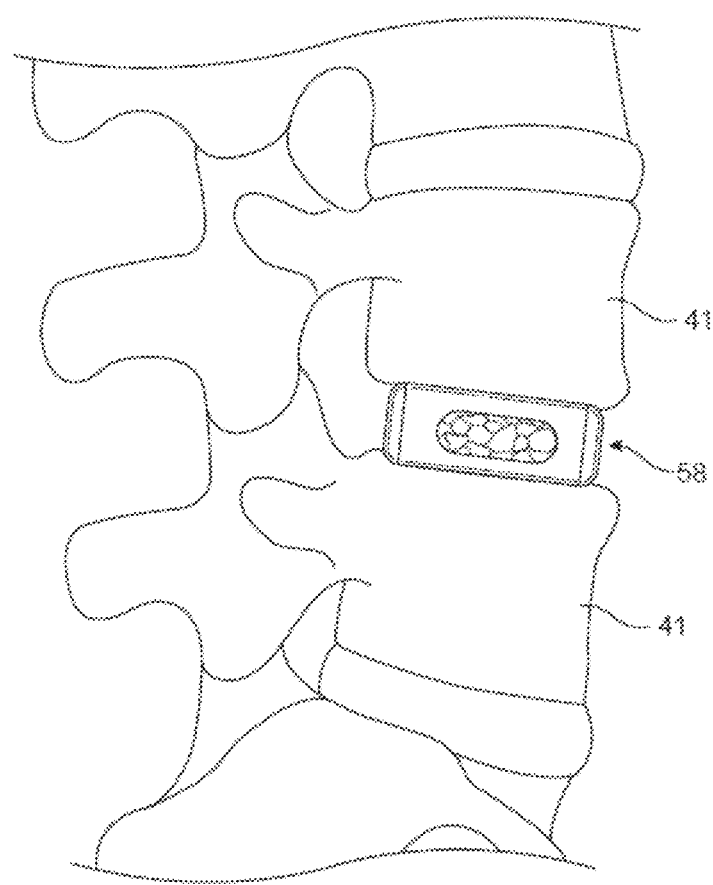
FIG. 5 is a schematic illustration of an interbody device after placement in the vertebral interspace.

FIG. 4 is a schematic illustration of the insertion of an interbody device 58 being placed into the intervertebral space 54. The interbody device 58 can be any such device and many different such devices are currently known and in use. Interbody devices may be cadaveric bone, autograft, allograft or a combination of synthetic materials and implants mentioned. Any adjuvant intradisc material could be used. This method may also be used across a disc space without any interbody implant. This method and device may be used to a) install an anterior construct using one or two pedicle screws per vertebral body, b) be used at one or more adjacent or non-adjacent spinal vertebral levels, the spinal vertebral levels may or may not be connected using an anterior stabilization device. Some levels may be connected with the anterior stabilization device spanning two or more spinal vertebral levels and other levels may only have an anterior construct at one level c) be used across a disc space level undergoing an interbody implant and/or fusion or across a disc space level not undergoing an interbody implant and/or fusion. In one aspect the interbody device 58 can have an outer casing 60 and an inner grafting material 64. The interbody device 58 can be manmade or fashioned from biomaterials such as cortical bone, cage and bone grafts, and the like. FIG. 5 is a schematic illustration, partially broken away, of the interbody device 58 after placement in the vertebral interspace device. In another aspect, the anterior and posterior stabilization devices may be used across a disc space having undergone artificial disc replacement as the interbody device 58 with or without being combined with a dynamic stabilization instrumentation system. The anterior or posterior constructs may be made of materials designed to allow simulated normal motion.

Figure 6:
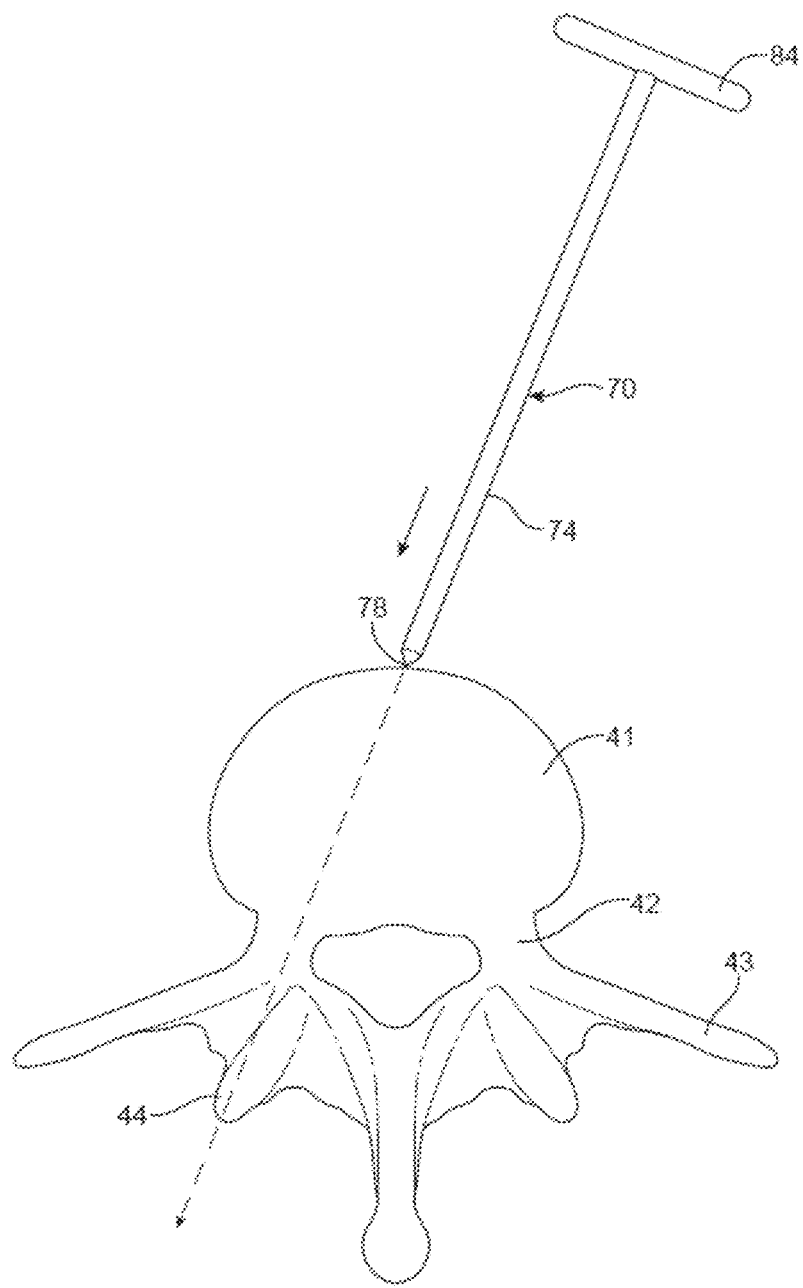
FIG. 6 is a schematic plan view of the placement of a Jamshidi type needle through the pedicle from an anterior approach

FIG. 6 is a schematic plan view of the placement of a cannulated bone needle or trocar 70 through the pedicle 42. Any suitable device for creating a passage through the pedicle of the vertebra and optionally also placing a guide wire in the passage is possible. Other methods for creating such a passage are also possible. Using the cannulated needle or trocar 70 the surgeon places the trocar on the anterior surface of the vertebral body, and can utilize a suitable intraoperative imaging system if desired. The trocar 70 is passed from the anterior surface of the vertebral body through the pedicle 42 and out the posterior portion of the vertebra into the surrounding soft tissue and muscle.

Figure 7:
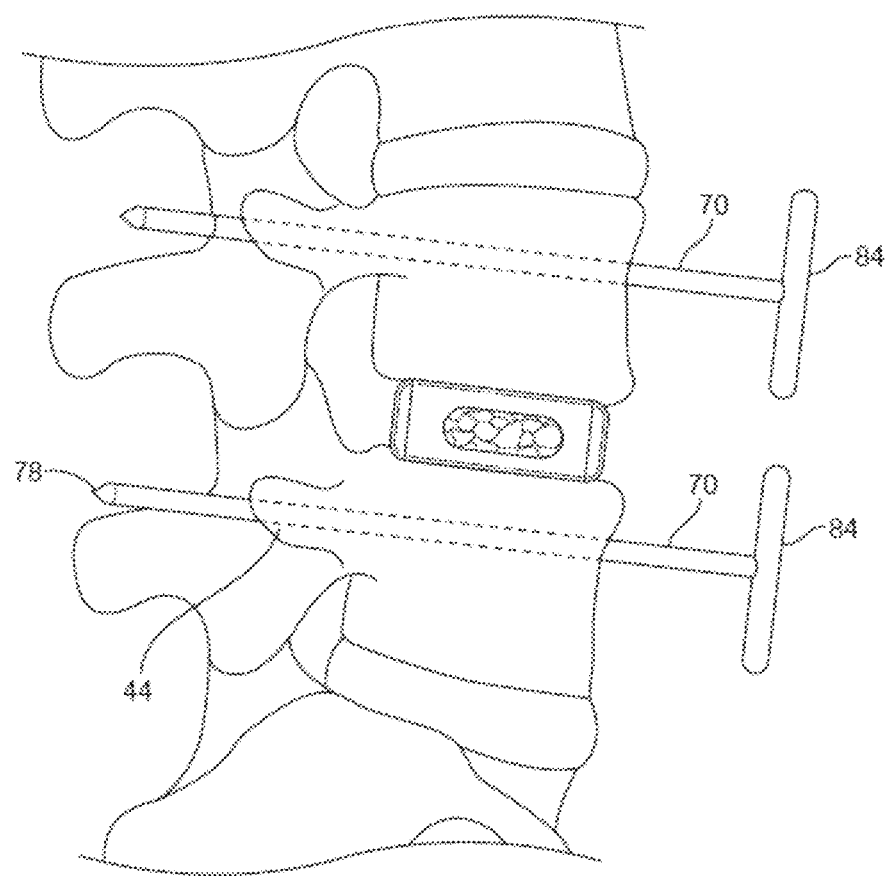
FIG. 7 is a schematic side elevation, partially in phantom, showing Jamshidi type needles after placement through two adjacent vertebrae.
Figure 8:
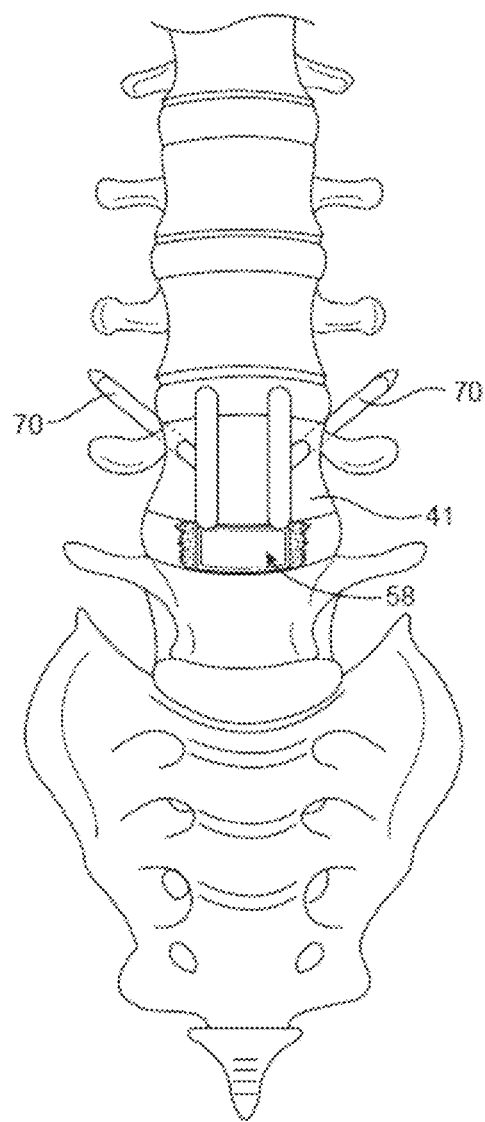
FIG. 8 is an anterior view.
Figure 9:
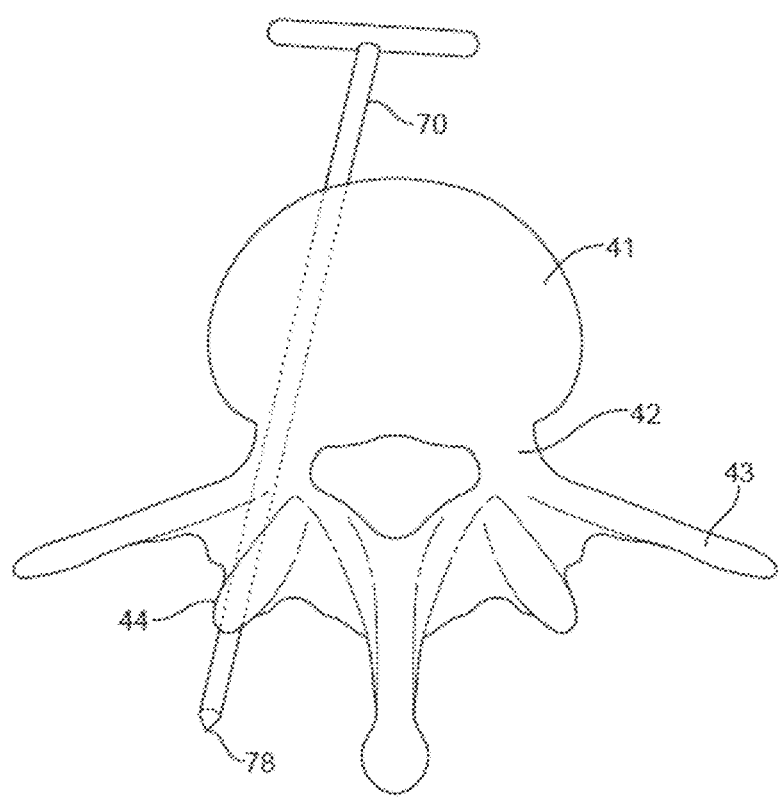
FIG. 9 is a plan view, partially in phantom.

In one example, a long (12-14") pedicle Jamshidi® (CareFusion Corp., San Diego, Calif.) type needle 70 having a shaft 74, pointed end 78, and a handle 84 for turning the needle can be provided. The needle 70 is directed toward pedicle 42 and out the posterior side of the vertebra and into soft tissue, as shown in FIGS. 7-9. In a procedure to stabilize the spine, a passage for a pedicle connector can be created in one or two locations for single vertebral use, and for stabilization across a disc space, there can be three or four locations, one or two in the superior vertebra 40 above the disc space 54 and one or two in the inferior vertebra 40' below.

Figure 10:
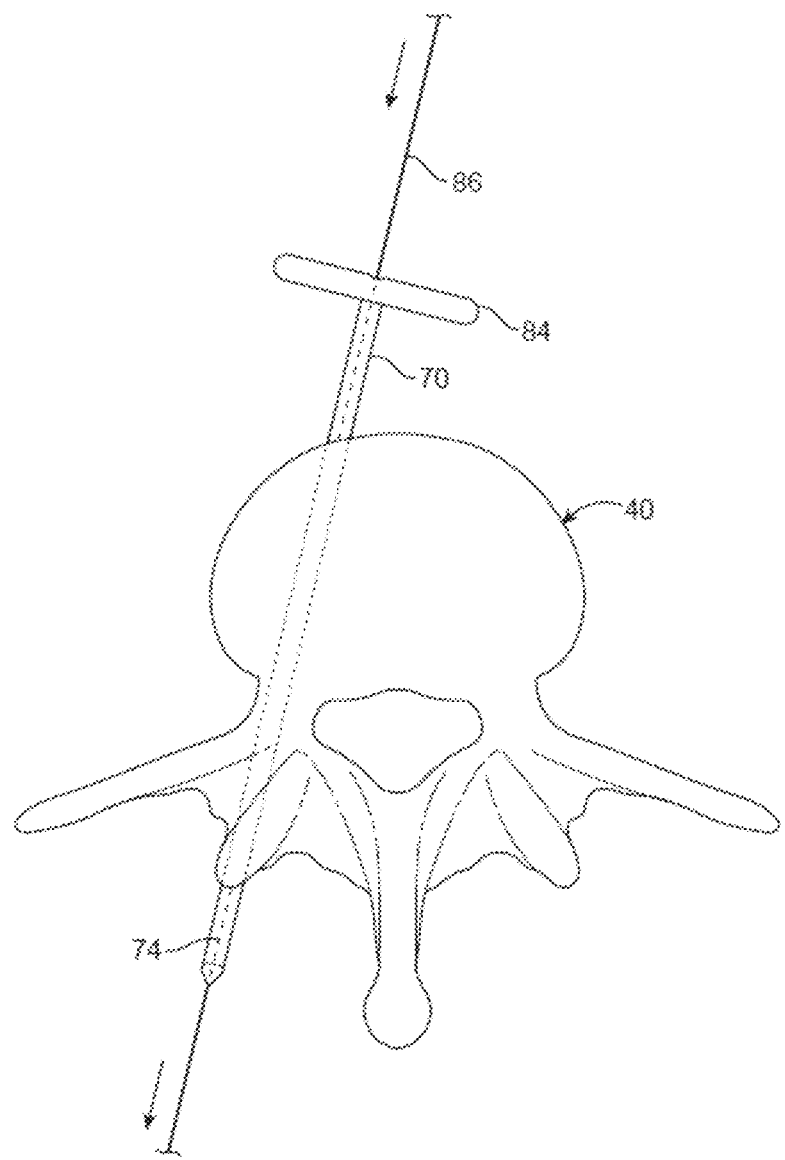
FIG. 10 is a schematic plan illustration of a vertebra with a Jamshidi type needle there through, and a guide wire placed through the needle.

A guide wire can be utilized to properly orient the procedure. Other localizing techniques and systems can also be used. FIG. 10 is a schematic plan illustration of a vertebra with a needle 70 there through, and a guide wire 86 placed through the cannula of the needle 70. The guide wire 86 is placed into the needle 70 and all the way through the vertebrae and into soft tissue on the posterior side of the vertebra 40. The needle or trocar 70 is then removed by pulling the trocar 70 anteriorly and leaving the guide wire in place.

Figure 11:
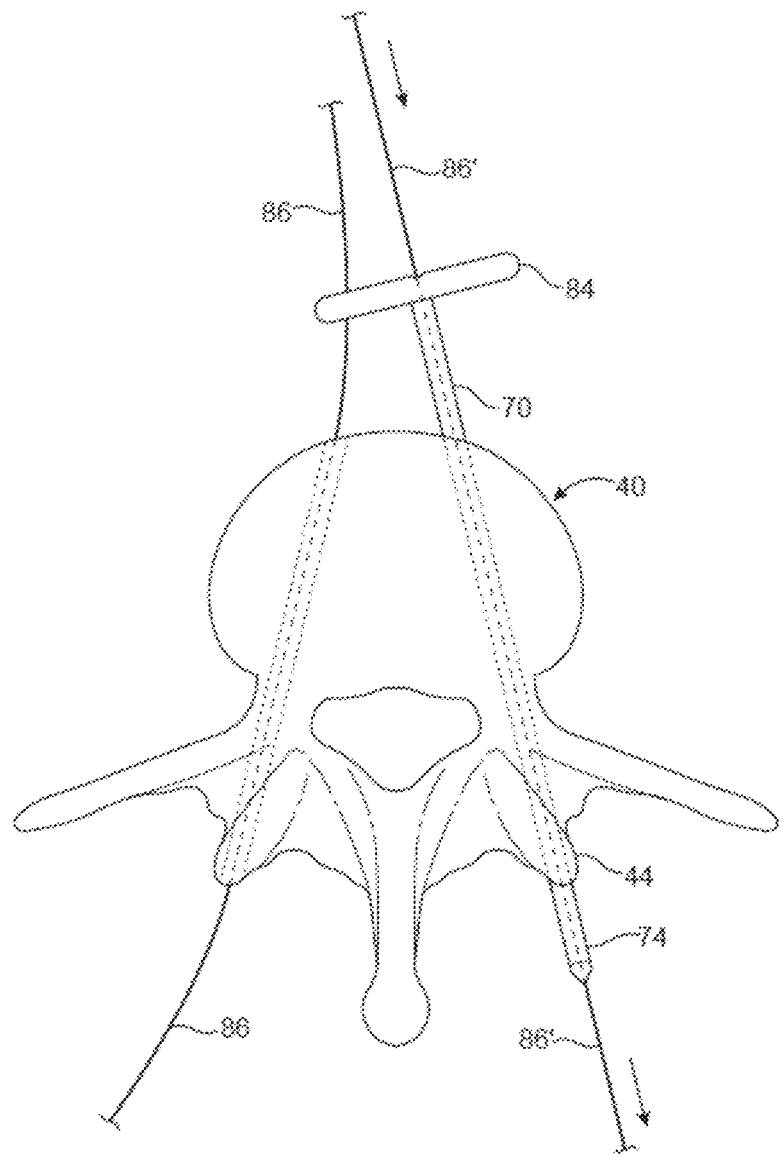
FIG. 11 is a schematic plan illustration of a vertebra with a guide wire in place and a Jamshidi needle placing a second guide wire through the vertebra.

This process is repeated across the midline on the opposite side of the vertebra and, in cases across a disc space, also repeated at the other vertebral levels involved in the stabilization. FIG. 11 is a schematic plan illustration of a vertebra with a guide wire 86 in place and a needle 70 placing a second guide wire 86' through the vertebra 40.

Figure 12:
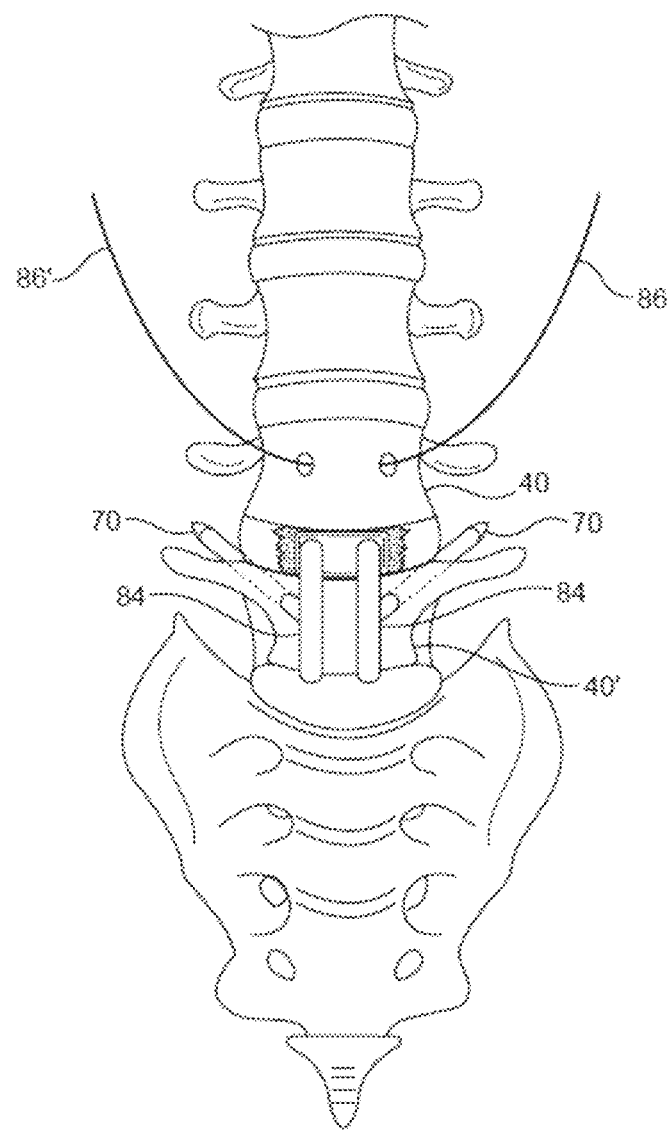
FIG. 12 is a schematic anterior view of a spine with two needles positioned through a vertebra at one level and two guide wires positioned through another vertebra at an adjacent level.
Figure 13:
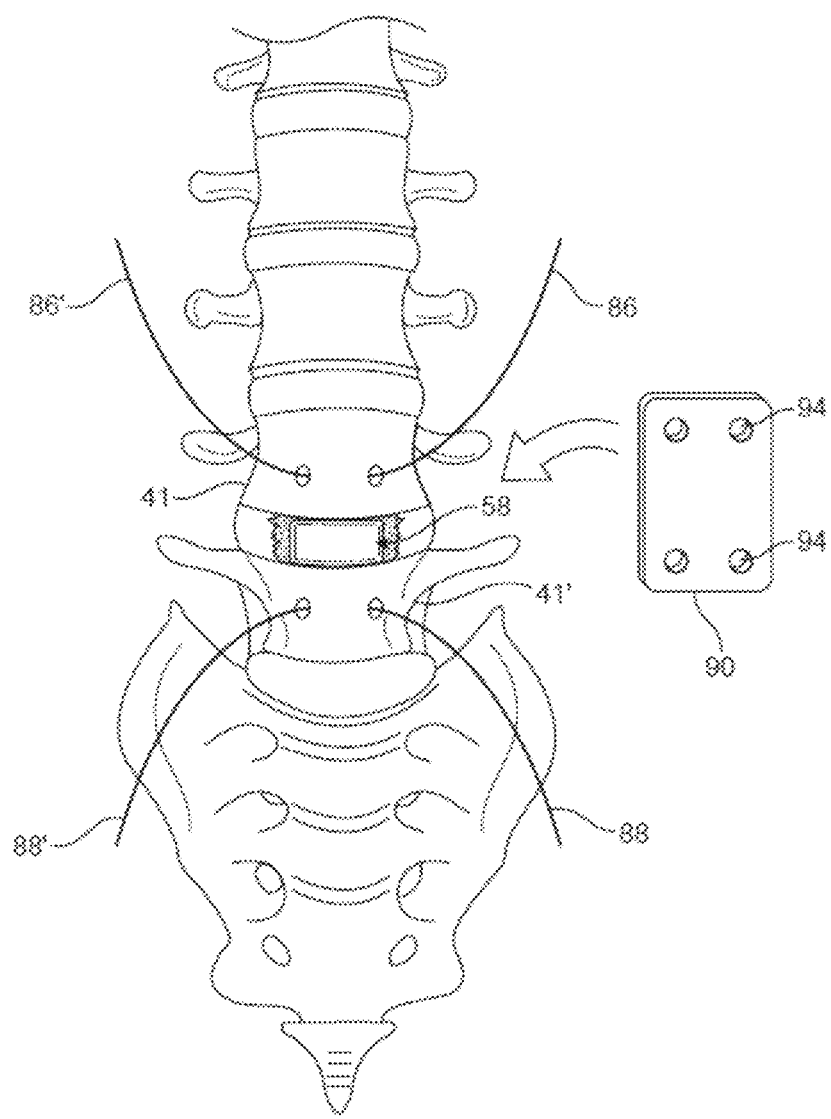
FIG. 13 is an exploded anterior view of a lumbar spine with guide wires positioned through adjacent vertebrae and an anterior stabilization construct for alignment with the guide wires.
Figure 14:
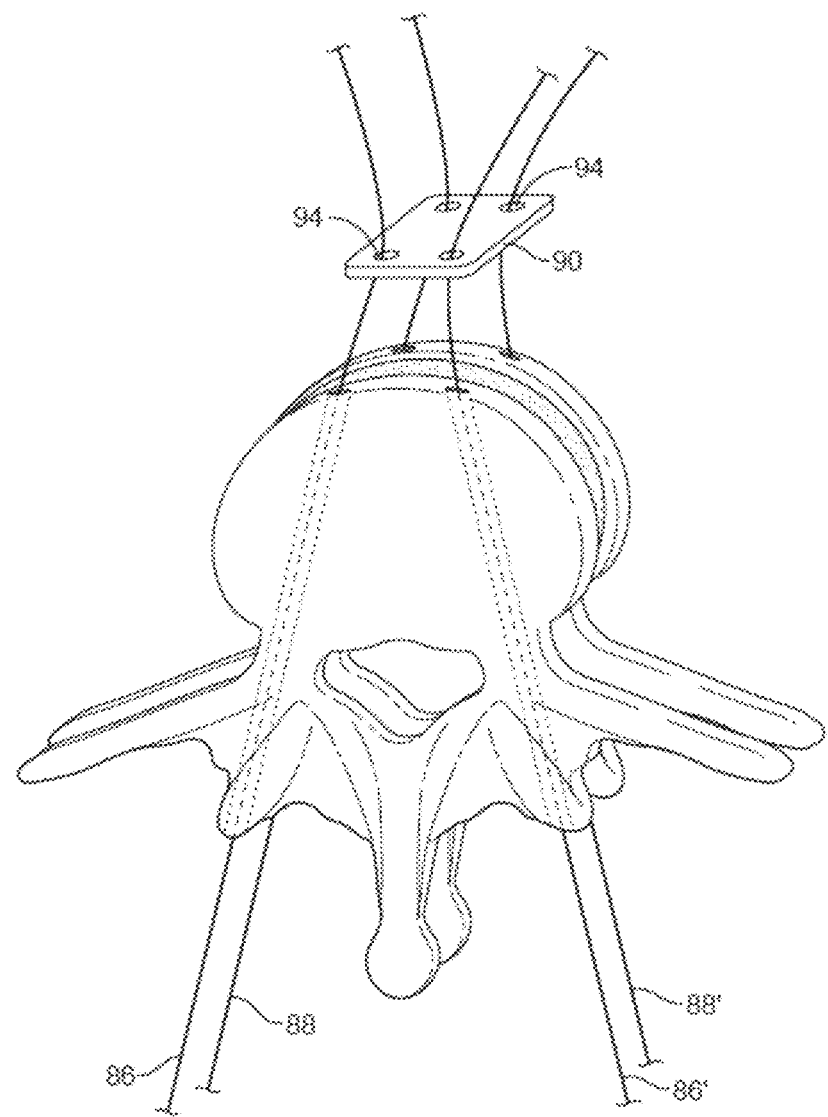
FIG. 14 is a schematic plan view, partially in phantom, of adjacent lumbar vertebrae with guide wires positioned through the vertebrae and an anterior stabilization construct positioned on the guide wires.
Figure 15:
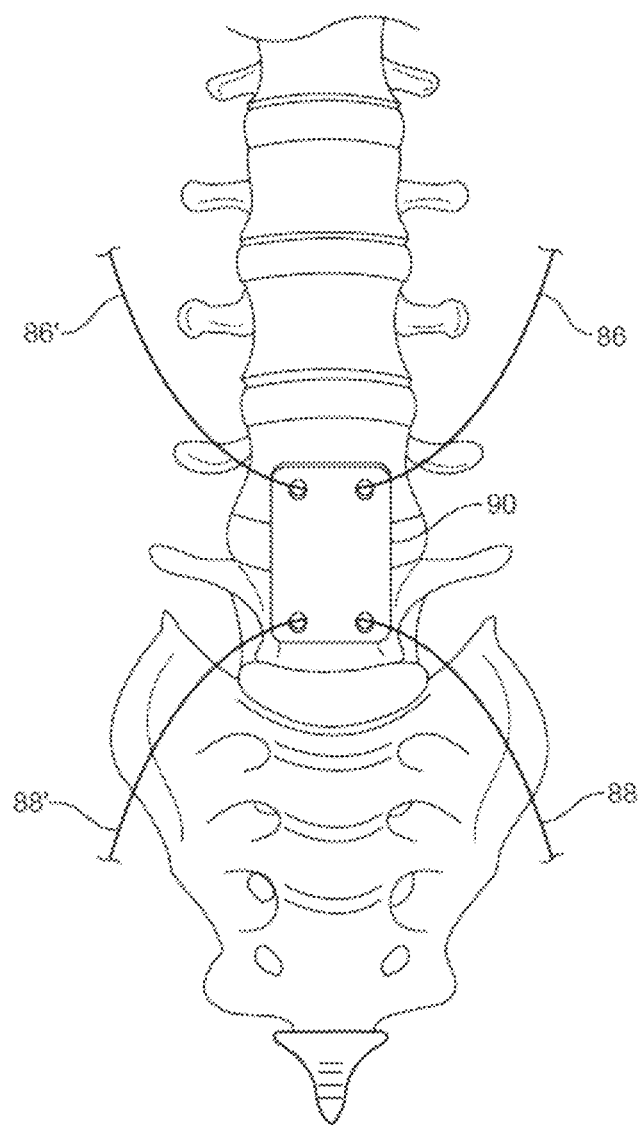
FIG. 15 is a schematic anterior view of a lumbar spine with guide wires positioned through adjacent vertebrae and an anterior stabilization construct positioned on the guide wires.

FIG. 12 is a schematic anterior view of a spine with two needles 70 positioned through a vertebra 40' at one (inferior) level and two guide wires 86 positioned through another (superior) vertebra 40 at another level. This results in the four or more wires being delivered through this anterior to posterior technique. FIG. 13 is an exploded anterior view of a spine with guide wires 86, 86' and 88, 88' positioned through adjacent vertebrae 40 and 40'. In this example the interspace has been treated with discectomy and interbody implant 58 placement An anterior stabilization construct 90 is provided and can be placed onto the guide wires 86, 86' and 88, 88'. The anterior stabilization construct 90 shown in FIG. 13 can have suitable structure such as apertures 94 for placement over the wires 86, 86' and 88, 88' such that the anterior stabilization construct 90 will be properly positioned adjacent to the spine. The anterior stabilization construct 90 is in this example a selected size plate, however, other types, sizes and shapes of anterior stabilization constructs are possible being made from materials of metallic, absorbable or synthetic nature or other commonly used biocompatible materials. In one aspect the interbody device and the anterior construct are a unit. The plate 90 can be sized based on the distances between the wires and the four wires 86, 86' and 88, 88' are passed through the corresponding holes 94 in the construct 90 as the plate is gently lowered onto the anterior surface of the vertebra, as shown in FIGS. 14-15.

Figure 16:
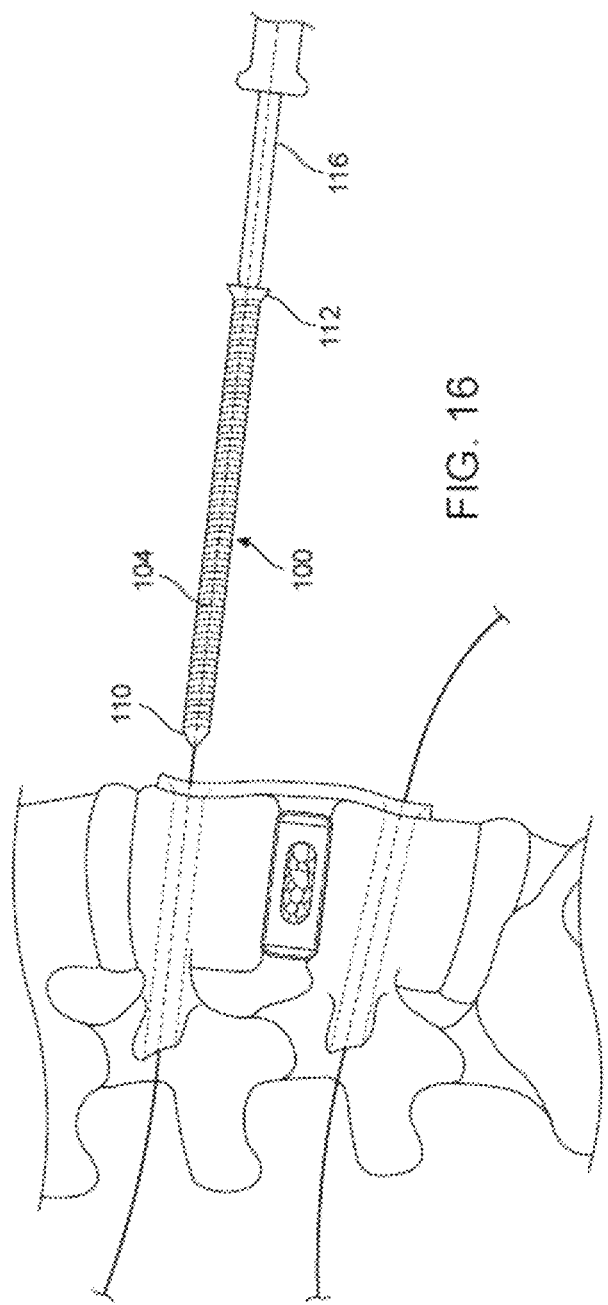
FIG. 16 is a schematic right side elevation, of a pedicle screw being passed over a guide wire and positioned for insertion into the vertebra with a cannulated screwdriver through a hole in the anterior stabilization construct.
Figure 17:
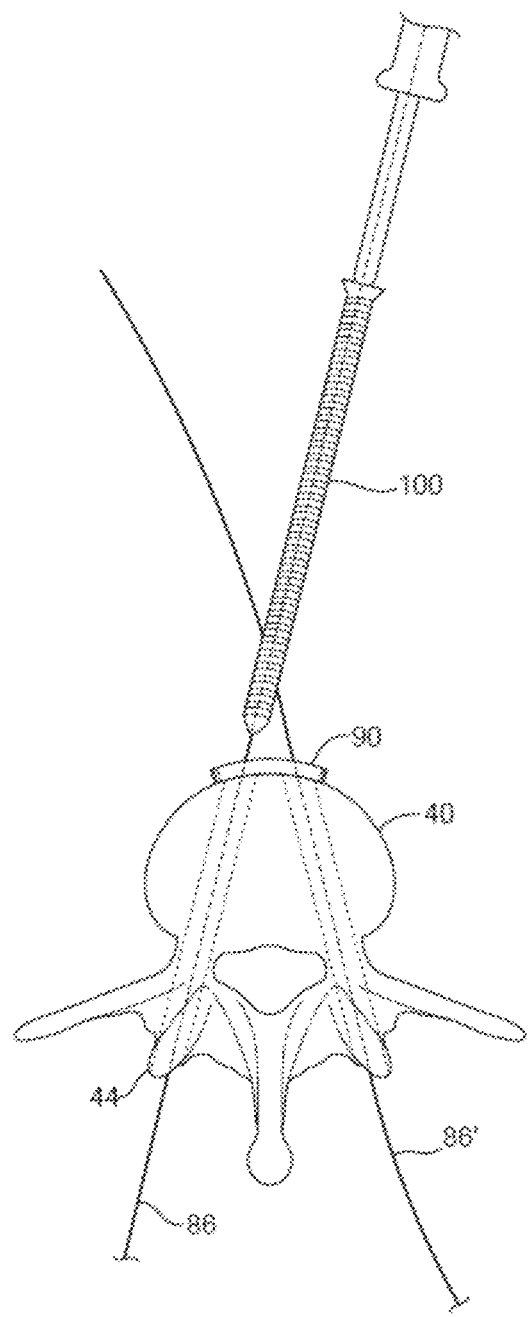
FIG. 17 is a schematic plan view, partially in phantom, of a vertebra with bilateral guide wires in place and anterior stabilization construct in place with a pedicle screw being positioned through the anterior stabilization construct and into the vertebra.
Figure 18:
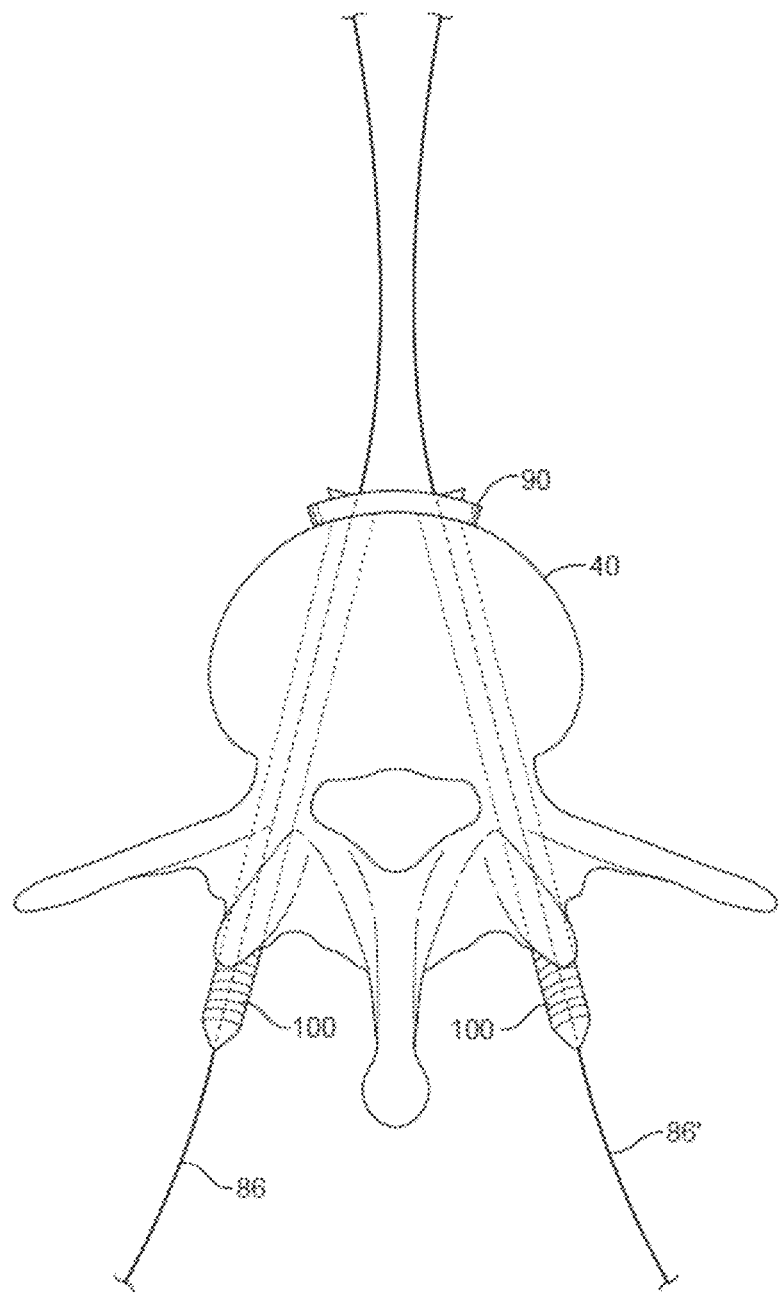
FIG. 18 is a schematic plan view, partially in phantom, of a vertebra with guide wires, anterior stabilization construct, and pedicle screws positioned in the vertebra with guide wires extending posteriorly into the muscle and soft tissue.
Figure 19:
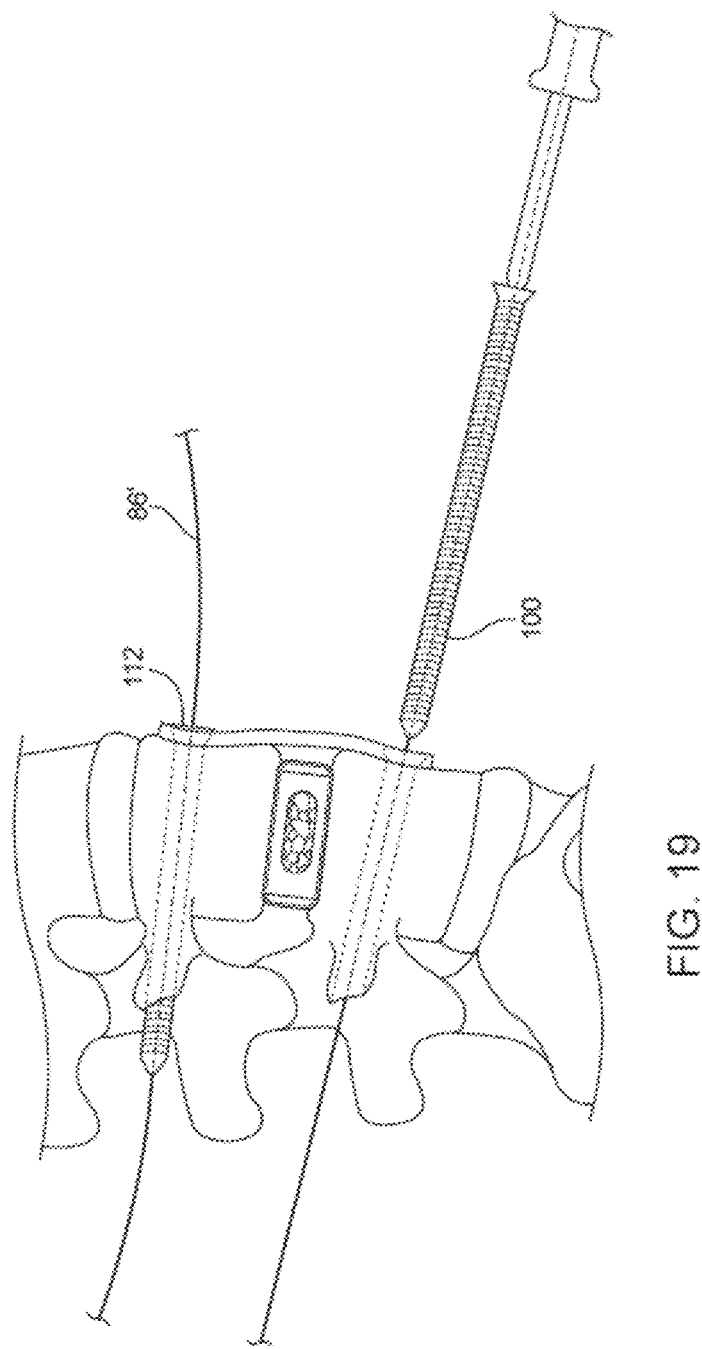
FIG. 19 is a schematic right side elevation, partially in phantom, of adjacent vertebrae with guide wires in place in the vertebrae, an anterior stabilization construct positioned adjacent to the vertebrae with the guide wires, and a pedicle screw in place at one level and another being placed at an adjacent level.

Once the anterior stabilization construct such as plate 90 is in place suitable structures such as a cannulated connector and cannulated driver such as a screw driver are selected and passed down the guide wire 86 and into the vertebral body 40 through the hole 94 in the anterior plate 90. A connector such as a pedicle screw 100 as shown in FIG. 16 can then be positioned through each passage that has been formed through the pedicle 42 of the vertebra 40. The pedicle screw 100 can have bone threads 104 for engaging bone surrounding the passageway through the vertebra. The pedicle screw 100 can have posterior end 110 and a head 112 at an opposing end. The pedicle screw 100 can alternatively be provided with other suitable structure for engaging a stabilization cap or head, such as set pins or other structure. As shown in FIG. 16, the pedicle screw 100 is positioned anterior to the vertebra 40, and the guide wire 86 is used to guide the pedicle screw 100 as it is driven by the cannulated screw driver 116 into the pedicle passageway of the vertebra 40. The pedicle screw 100 is turned driving the screw along the path of the wire through the vertebral body, through the pedicle 42 and out the posterior portion of the vertebra into the soft tissue and muscle. The screw head 112 can engage the anterior plate 90 or other anterior construct in a countersink relationship or other suitable relationship. The anterior construct 90 may have a pedicle screw locking mechanism. The locking mechanism to secure the screws 100 to the plate 90 may be one of many possible locking mechanisms involving set screws over the heads of each pedicle screw 100 or a head expanding set screw system to lock the plate 90 or other construct to the pedicle screw 100. Other locking mechanisms may also be used. The locking mechanism may be a ring type locking mechanism. Other acceptable locking mechanisms that block the pedicle screw from backing out of the vertebra or dislodging from the plate may be used. This process is repeated for each of the wires at the same level (FIGS. 17-18) and at different levels (FIG. 19) until all desired wires 86, 86' and 88, 88' and corresponding pedicle screws 100 have been placed. In the illustrated example four pedicle screws 100 are used.

Figure 20:
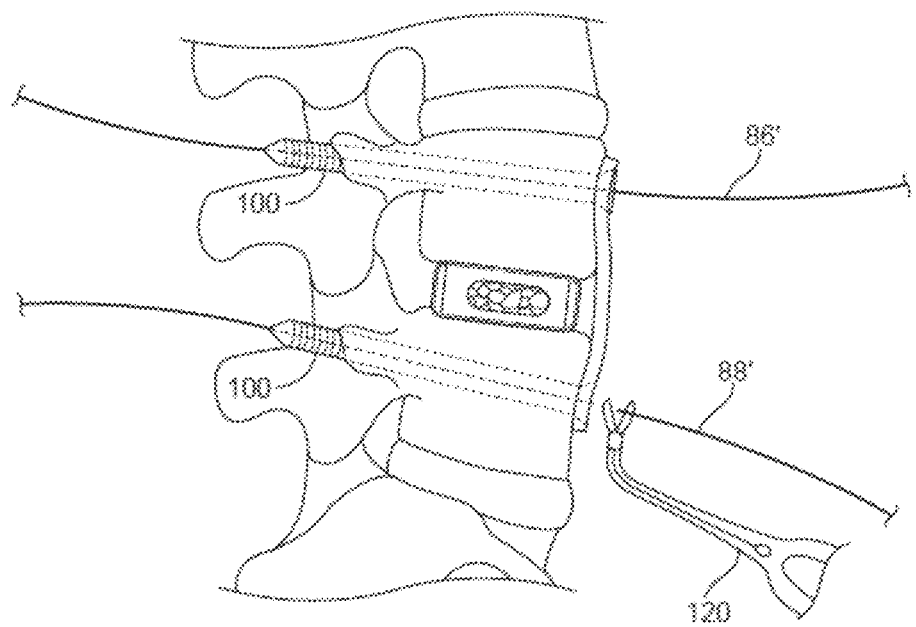
FIG. 20 is a schematic right side elevation, partially in phantom, of guide wires being cut at the level of the anterior stabilization construct after pedicle screws have been positioned in adjacent vertebrae.
Figure 21:
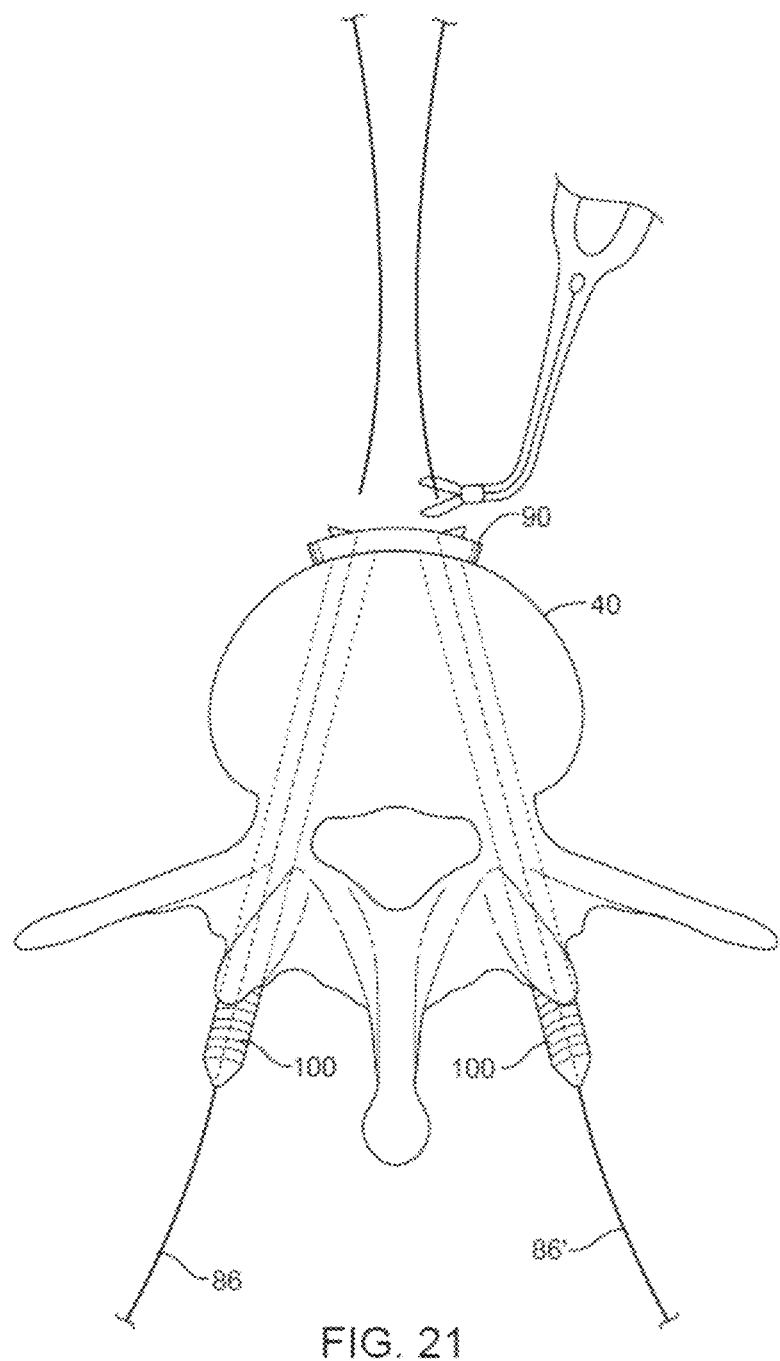
FIG. 21 is a plan view of FIG. 20.
Figure 22:
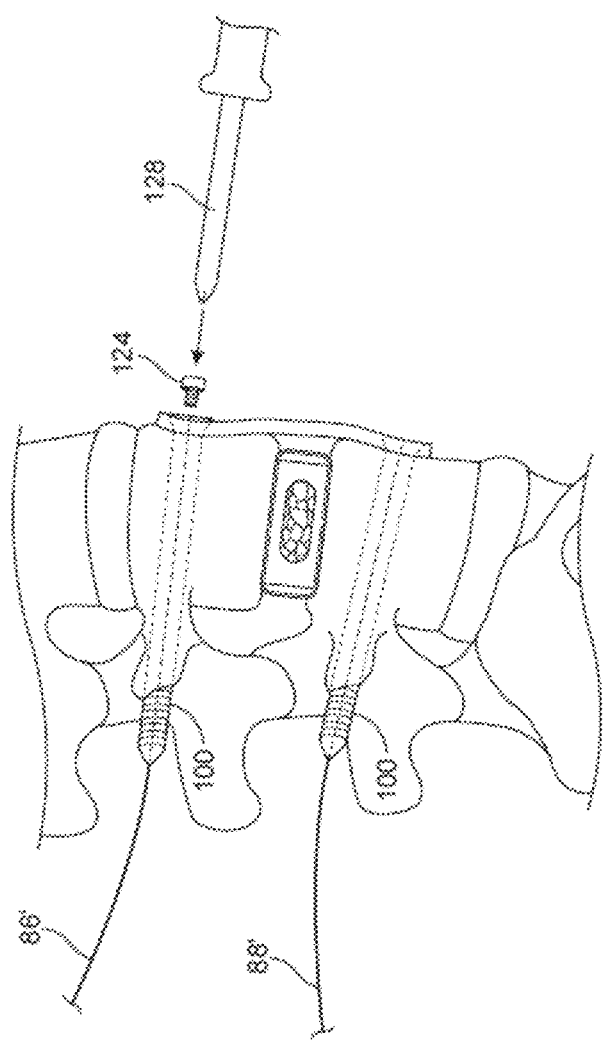
FIG. 22 is a schematic right side elevation, partially in phantom, of guide wires being secured inside the pedicle screws with set screws placed into the head of the pedicle screw.
Figure 23:
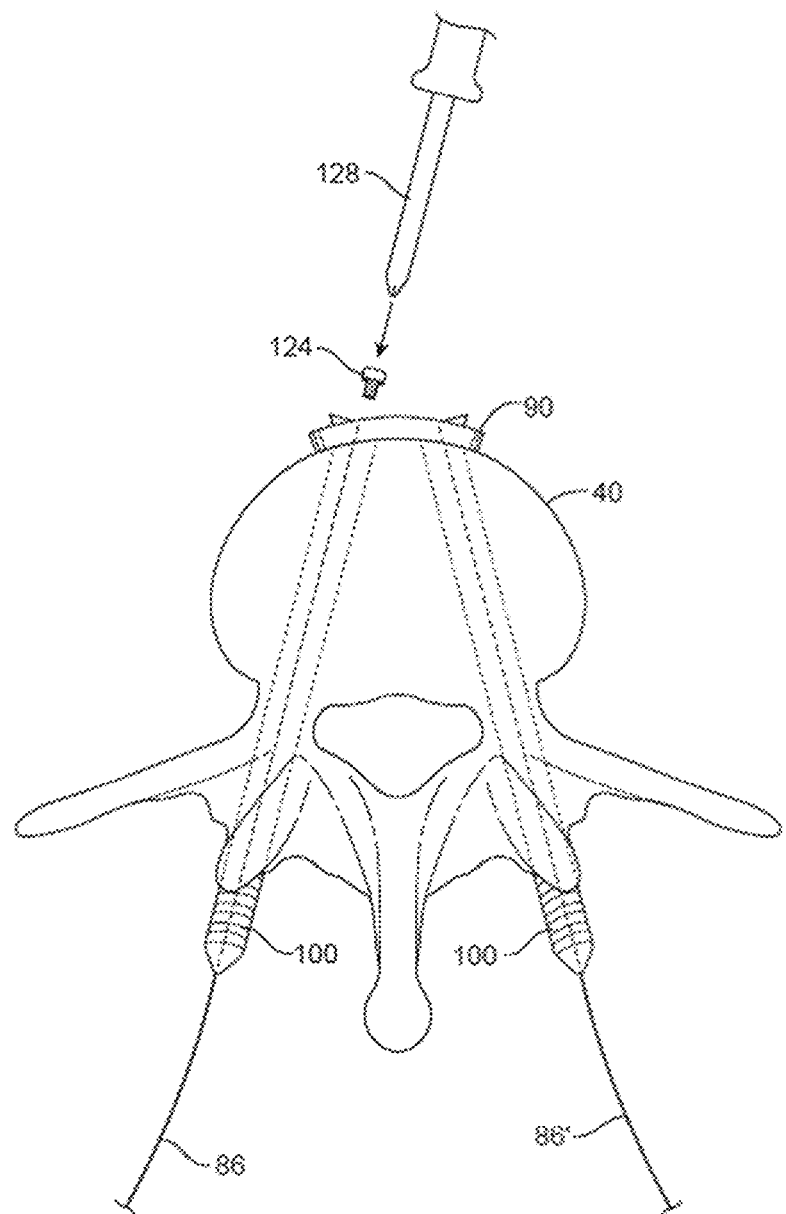
FIG. 23 is a plan view of FIG. 22.

Once the position of the pedicle screws 100 has been found to be satisfactory the guide wires on the anterior side of the vertebrae can then be cut and the ends secured inside the pedicle screw by locking screws 124. FIGS. 20-21 illustrate the use of wire cutter 120 to cut the guide wires after pedicle screws 100 have been positioned in the vertebrae 40 and 40'. The anterior ends of the wires are then secured, as shown in FIGS. 22-23. FIGS. 22-23 illustrate guide wires 86 and 86' (FIG. 22), and 86' and 88' (FIG. 23) being secured to the pedicle screws 100 with locking screws 124 using an appropriate screw driver 128. The locking screws 124 screw into cooperating threads at screw head 112 to secure the wire inside screw head 112, closing the cannulated portion of the pedicle screw 100 on the anterior end of the wire.

Figure 24:
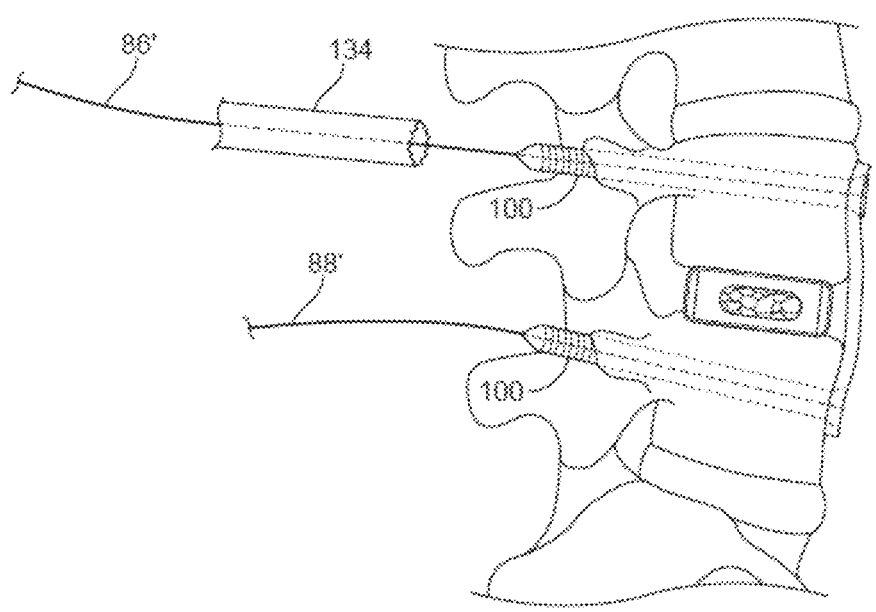
FIG. 24 is a schematic right side elevation, partially in phantom, of a spine showing the use of a cannulated reamer to expose the posterior ends of the plating screws.

Once all desired pedicle screws 100 are in place, four in this example, the patient is closed from the anterior approach and carefully turned into the prone position with guide wires inside the screw and projecting into the soft tissue. Once in the prone position intraoperative imaging identifies the location of the required skin incisions to gain access to the guide wires. These incisions may be on either side of the midline for paramedian incisions typically used for minimally invasive techniques, or a midline incision can be used for open techniques. The incisions are made and the dissection is performed using standard surgical techniques down to the end of the wires. The wire tips are located in the soft tissue and a cannulated reamer 134 or other suitable device can placed over the wires to prepare a channel down to the posterior ends of the pedicle screws 100, as shown in FIG. 24.

Figure 25:
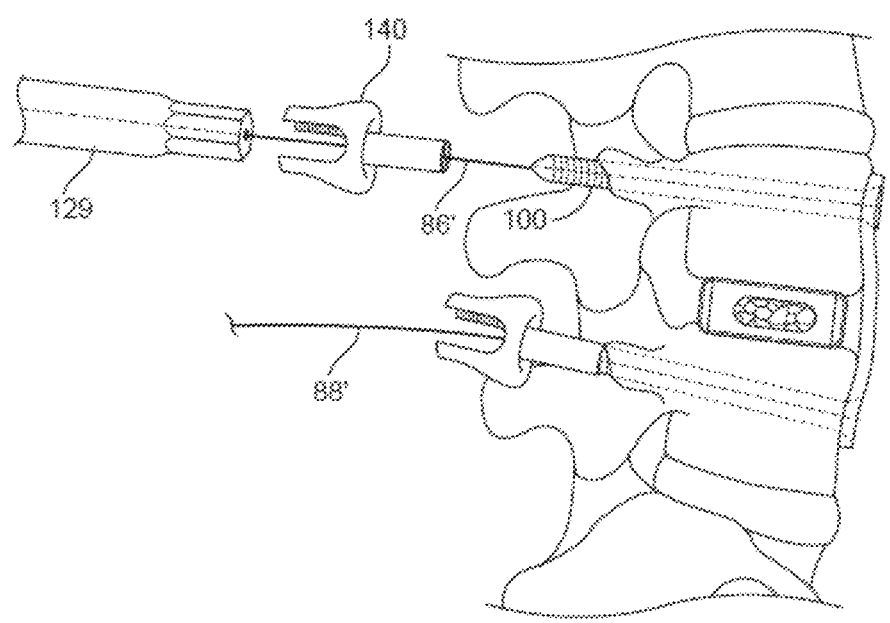
FIG. 25 is a schematic right side elevation, partially in phantom, showing the threaded placement over a guide wire of cannulated stabilization caps onto the posterior ends of the pedicle screws.
Figure 26:
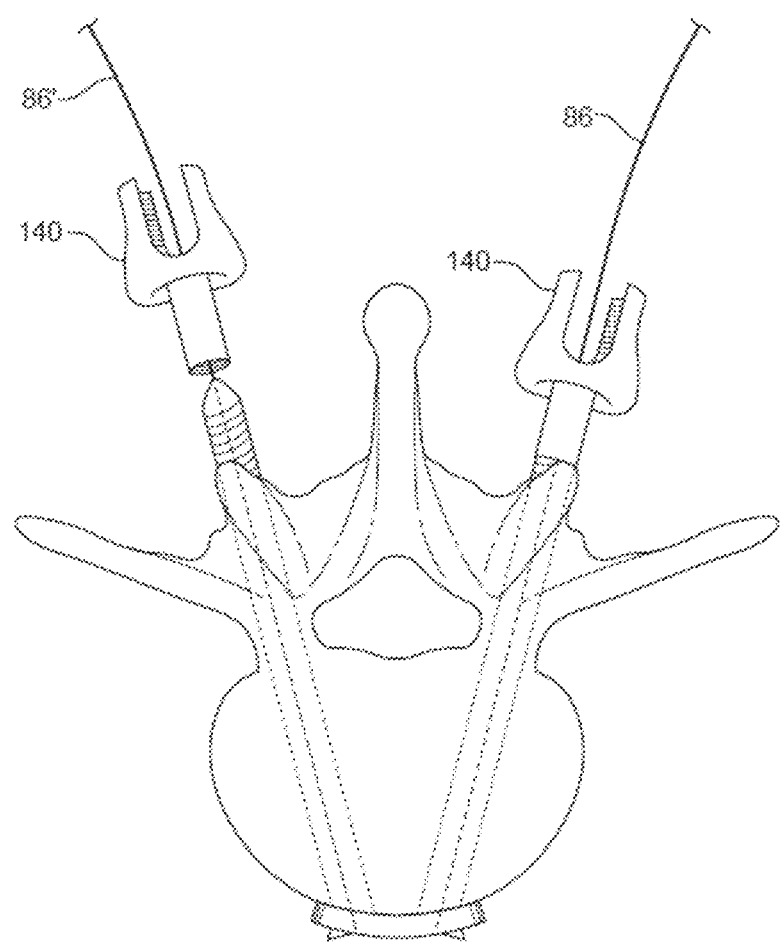
FIG. 26 is a schematic plan view of a vertebra, partially in phantom, of stabilization caps each being positioned onto the guide wires attached to the posterior ends of pedicle screws and one being threaded down onto the pedicle screw.
Figure 27:
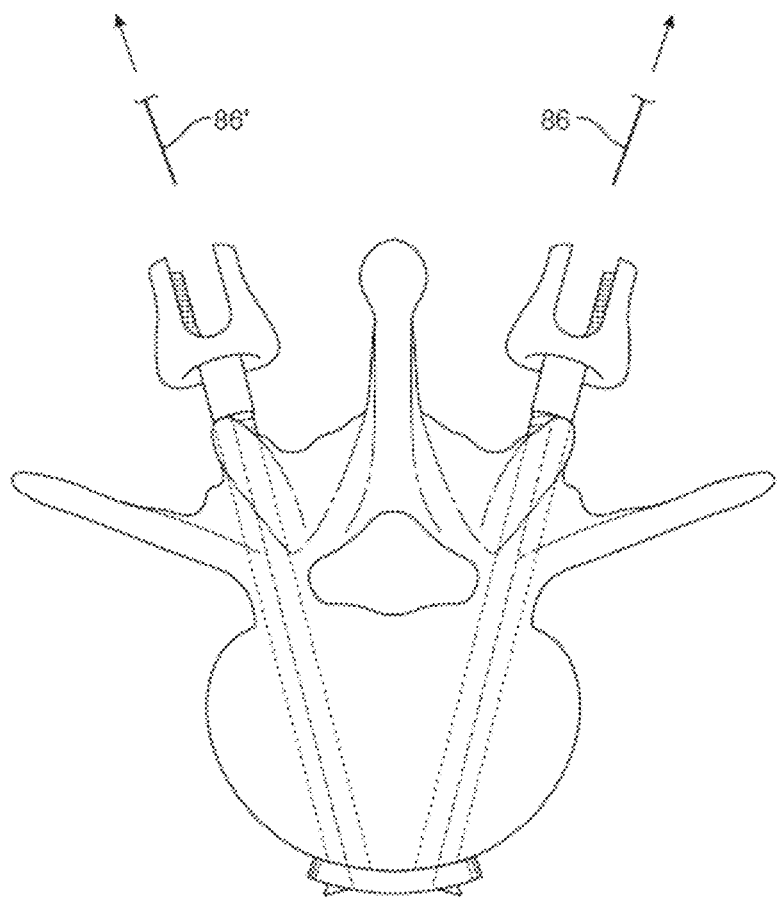
FIG. 27 is a schematic plan view of a vertebra, partially in phantom, of screw heads being attached to the posterior ends of pedicle screws and the guide wires are seen being removed posteriorly.

FIGS. 25-26 illustrate the placement of cannulated stabilization heads or caps 140 onto the wires emerging from the posterior ends of the pedicle screws 100 using a suitable screwdriver 129. Cannulated stabilization caps 140 or other fasteners are placed over wires 86', 88' and threaded down on top of pedicle screws 100. The cap 140 is then turned with the assistance of a suitable device such as screw driver 129, (FIG. 27) securing the cap 140 to the pedicle screw 100. For open incisions the stabilization caps may be manually placed either directly on the pedicle screw tips for non-guide wire cases or over the exposed wires and tightened with the cannulated screwdriver 129. Once the caps have been installed through either minimally invasive technique or traditional open incision, the guide wires 86, 86' and 88, 88' are then removed by manually pulling them posteriorly out of the surgical area.

In one embodiment of the invention the stabilization cap 140 is a variable angle device and in another embodiment it is a universal stabilization cap with threaded linkages either on the outer edge or on the inner surface so as to engage multiple different types of posterior stabilization systems. Other stabilization cap designs are possible.

Figure 28:
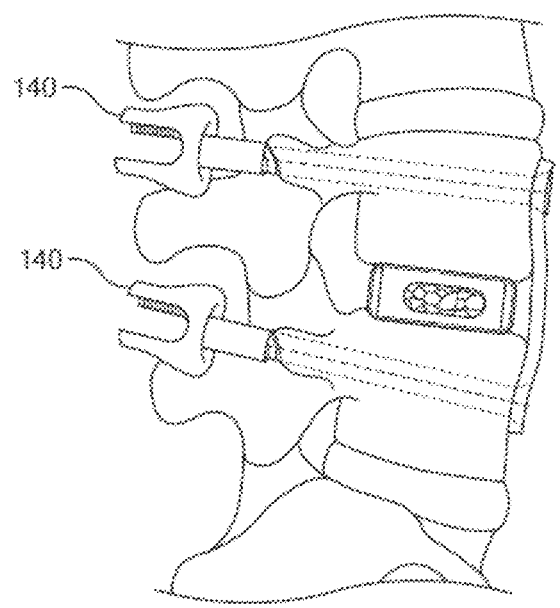
FIG. 28 is a schematic right side elevation, partially in phantom, of the system after removal of the guide wires.
Figure 29:
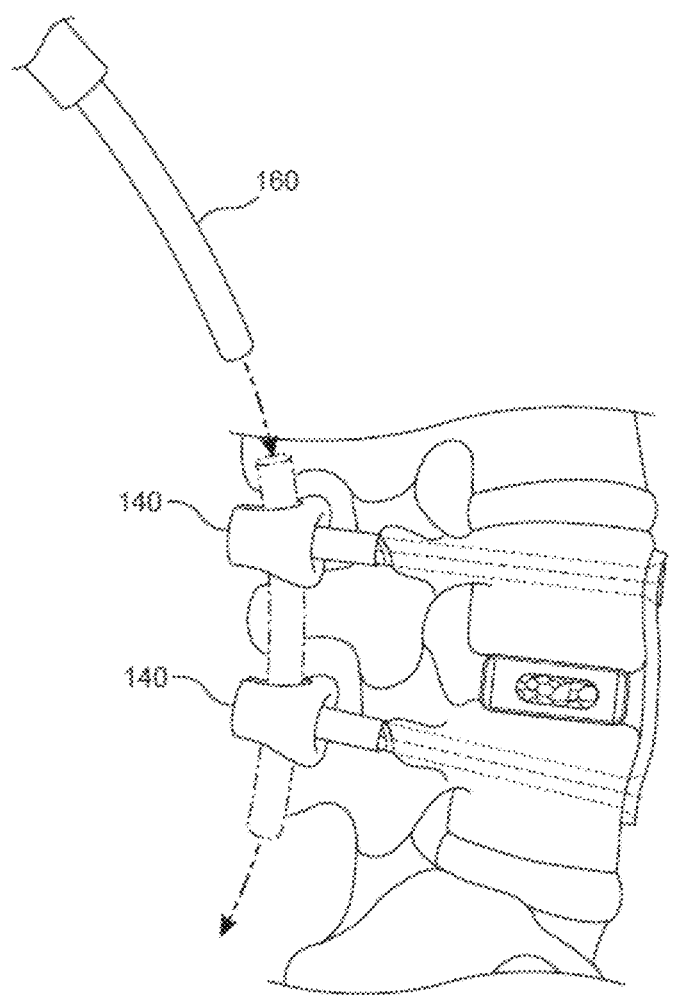
FIG. 29 is a schematic right side elevation, partially in phantom, after anterior stabilization construct, interbody implant and pedicle screws with stabilization caps have been installed, and a minimally invasive rod designed to pass under the skin and muscle layer between the ipsilateral pedicle screw stabilization caps is seen being passed from rostral to caudal through the stabilization cap connectors prior to tightening.
Figure 30:
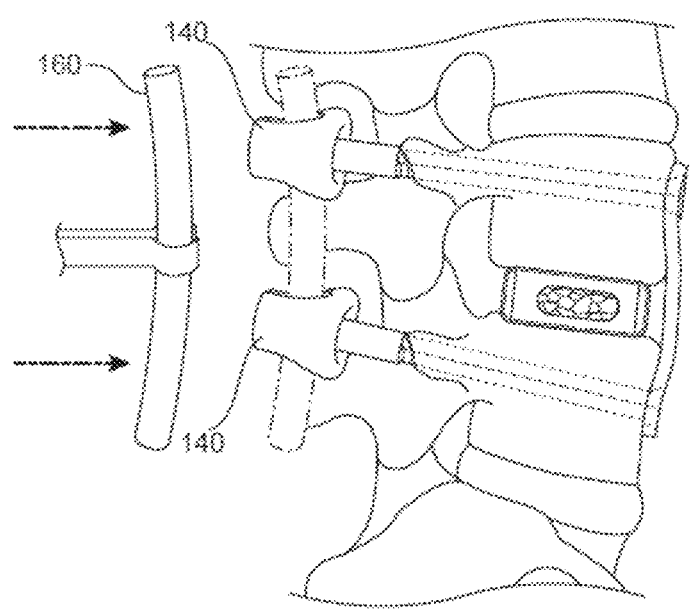
FIG. 30 is a schematic right side elevation, partially in phantom, showing the application of a connecting rod between ipsilateral stabilization caps using an open, non-minimally invasive technique.

FIG. 28 is a schematic right side elevation, partially in phantom, of the stabilization caps applied to the posterior ends of the pedicle screws 100 in a four pedicle screw, adjacent vertebral level, interbody device example. FIG. 29 is a schematic right sided elevation, partially in phantom of percutaneous connector rod 160 being passed under the skin and into alignment with two ipsilateral stabilization caps 140 prior to being locked in place. FIG. 30 is a schematic right sided elevation, partially in phantom of an example of the placement of the connector rod 160 into alignment with two ipsilateral stabilization caps 140 through an open posterior incision technique.

Figure 31:
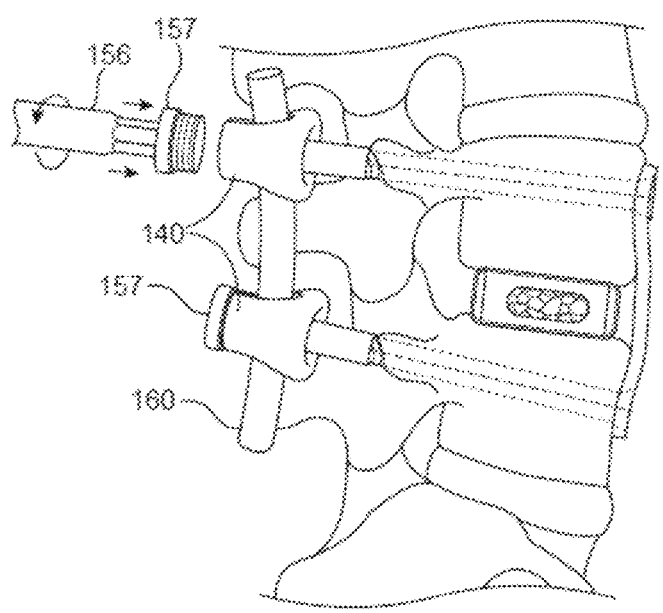
FIG. 31 is a schematic right side elevation, partially in phantom, showing the connecting rod being tightened down to the stabilization caps by application of a set screw with a driver.

FIG. 31 is a schematic right side elevation, partially in phantom of the anterior and posterior constructs in place. A set screwdriver 156 is seen placing a locking set screw 157 into the stabilization cap head which, upon tightening, locks the connector rod in place.

In the preferred embodiment of the invention the stabilization caps 140 are applied with a locking extender and the wires removed through the extender. A connecting rod is then fashioned and placed percutaneously connecting the screw heads and allowing set screws to be passed through the extenders and locked into position fixing the rod to the pedicle screw system. During the tightening phase either distraction or compression may be used. The pedicle screws 100 may be in either a variable angle relationship with the anterior construct or a fixed angle relationship with the anterior construct.

Figures 32A, 32B:
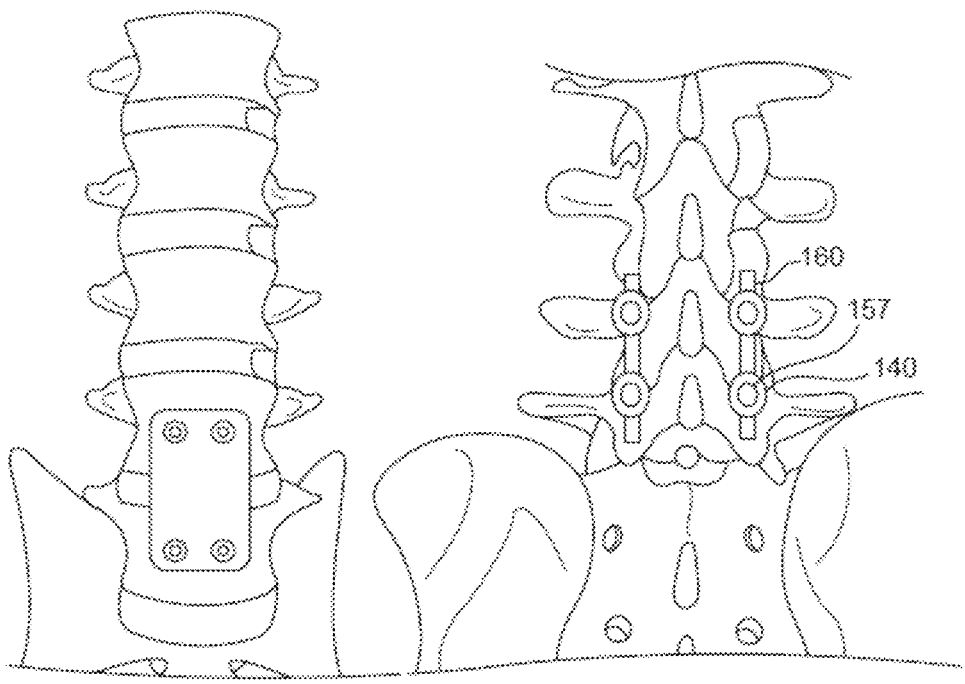
FIG. 32 (A-C) is an A) anterior view, B) posterior view, and C) right side elevation with partial phantom of the assembled system.
Figure 32C:
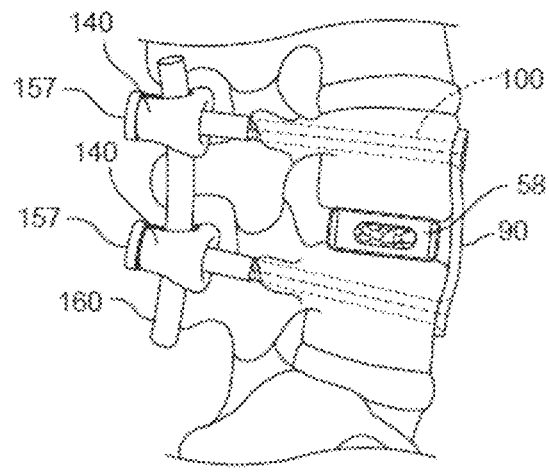

FIG. 32 (A-C) is an A) anterior view; B) posterior view; and C) right side elevation of a spinal stabilization assembly example crossing a disc space and using an interbody implant positioned on a spine. The invention combines the advantages of both anterior as well as posterior surgical techniques and significantly reduces the risk of hardware failure from screw pullout as the stabilization system does not rely solely on the relationship between the pedicle screw threads and the bone density itself. The anterior stabilization construct such as plate 90 and posterior stabilization construct such as rod 160 are securely connected directly together and through the bone to form a very secure spine stabilization assembly.

Figure 33:
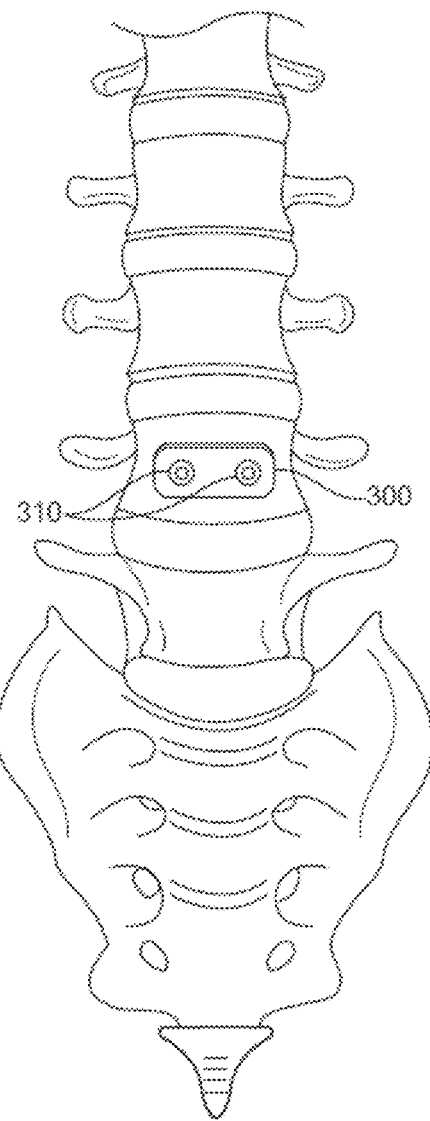
FIG. 33 is an anterior view of an alternate anterior construct for use without interbody grafting positioned on a lumbar spine.

FIG. 33 is a schematic anterior view of the lumbar spine with an example of a one level anterior construct 300 held in place by two pedicle screws 310. In other examples such a one level construct could be held in place by one pedicle screw.

Figure 34:
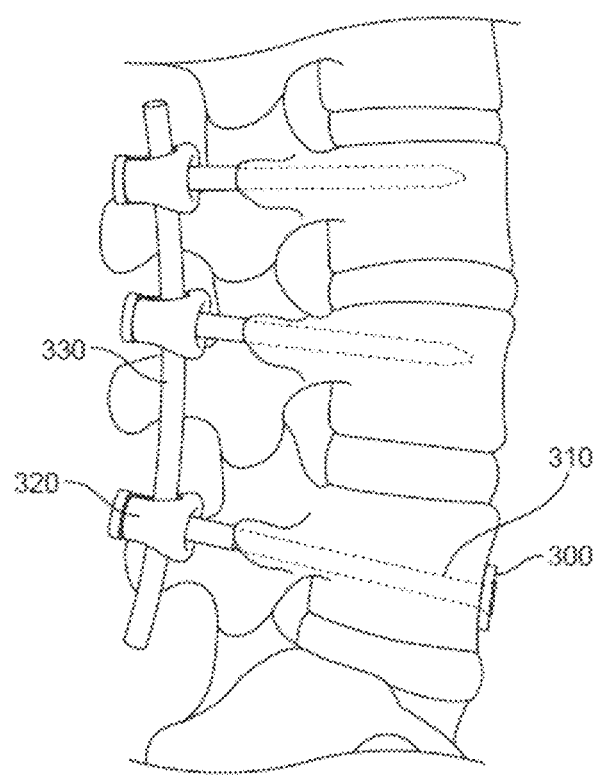
FIG. 34 is a schematic right side elevation, partially in phantom, of an alternate embodiment where the anterior pedicle screw system is comprised of an anterior construct and serves as the caudal portion of a combined multiple level stabilization system.
Figure 35A:
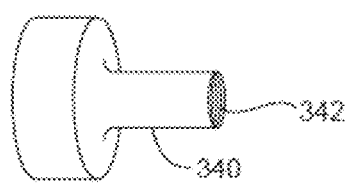
FIG. 35 (A-D) is a schematic representation of A) an alternate version of a stabilization cap, B) an exploded view of the stabilization cap with a posterior loading U-connector, C) the assembled posterior loading U-connector and stabilization cap, and D) exploded view of stabilization cap and a side loading U-connector.
Figure 35B:
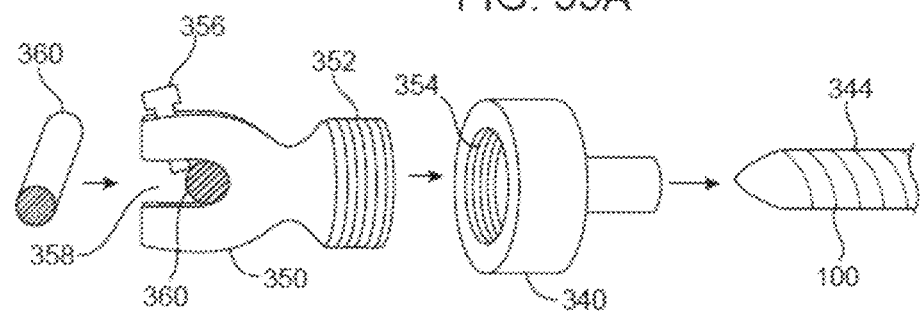
Figure 35C:
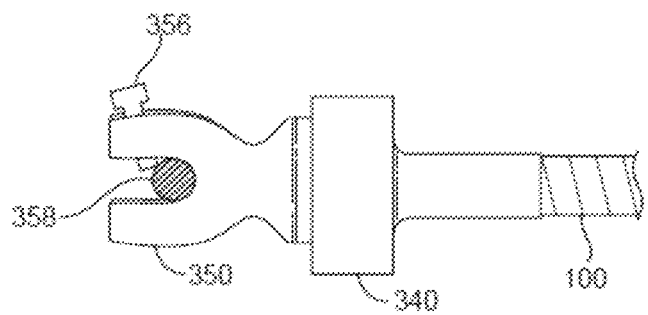
Figure 35D:
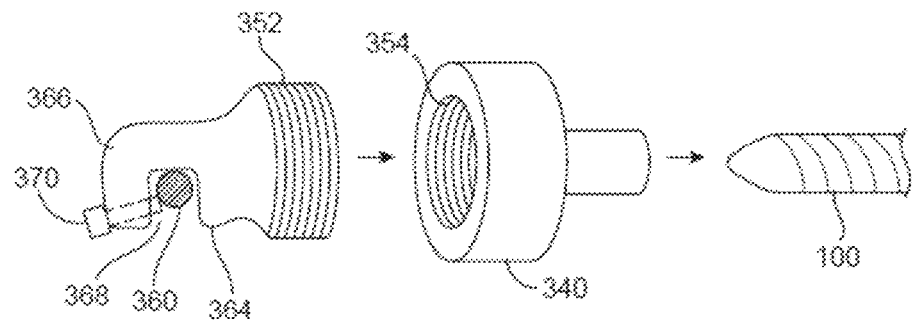

FIG. 34 is a schematic right side elevation, partially in phantom showing an example of how this system can be used as the single vertebral level pedicle connector 310 anchoring anterior construct 300 in a multilevel stabilization surgery where the others levels are pedicle screw instrumentation using conventional posterior pedicle screw placement techniques. The stabilization caps 320 used and the connector rods 330 used may be compatible.

The materials forming the components of the system can be any suitable surgical grade materials. In the preferred embodiment the components are made of metals such as titanium, cobalt/chrome, stainless steel or other alloys or metals, synthetic materials such as polyaryletherketone (PAEK), polyetheretherketone (PEEK), and also certain bioabsorbable materials such as polylactate are possible.

FIG. 35 (A-D) is a diagram of alternate embodiments of the stabilization caps and rod connectors. The universal stabilization cap 340 can be used to thread together a U-shaped rod connector 350 and allow threaded attachment to the pedicle screw 100 by threads 342. The threads 342 cooperate with threads 344 on the pedicle screw 100. The U-connector 350 can have threads 352 for engaging threads 354 on stabilization cap 340, or other suitable engagement structure. The U-connector 350 can have a posterior facing groove 358 for receiving stabilization structure such as rod 360 or other suitable stabilization structure. A set screw 356 can be used to secure the rod 360 in place. The U-connector may, in another example, be a side loading rod connector 364 having an arm 368 defining a groove 368 for receiving the rod 360. The side loading connector 364 can be attached to the universal stabilization cap 340 by threads 352. The U-connector devices hold the rod in place by set screws 370.

FIG. 36 (A-C) is an exploded side elevation of an alternative embodiment of a pedicle screw 400 used in this system. The pedicle screw 400 comprises an anterior part 404 that is separable from a posterior part 408. The anterior part 404 has a tubular body with a central passageway for receiving a guide wire and a head 416 for engaging the anterior stabilization construct. The anterior part 404 also has external threads 428 for engaging bone as the screw is advanced through the vertebra. The posterior part 408 has a tubular body with a central passageway for receiving the guide wire and external threads 420 similar to the external threads 428 of the anterior part 404 for engaging bone as the screw 400 is advanced through the vertebra. The anterior part 404 and posterior part 408 have suitable structure for detachably joining the two parts together. In one aspect, the posterior part 408 has a threaded extension 430 with threads 434 which mate with corresponding female threads 438 on an interior portion of the anterior part 404. The central passageway of the anterior part 404 aligns with the central passageway of the posterior part 408 to permit a guide wire to be passed through the screw 400. An opening 440 in tip 410 of posterior part 408 permits the guide wire to exit the screw. Slots 442 or other structure can be provided to permit the turning of the posterior part 408 with a screw driver or other similar structure to remove the posterior part 408 from the anterior part 404. This system permits adjustment by engaging the slots 442 with a screwdriver and turning the posterior part 408 to separate the posterior part 408 from the anterior part 404 of the screw 400. This configuration of the screw 400 allows for revision of the system independently without the requirement of both an anterior and posterior surgical exposure. For anterior revisions, the anterior construct would be exposed and the screws 400 turned with a screwdriver. The screw 400 would then separate from the posterior portion and allow removal of the entire anterior construct without requiring a posterior dismantling of the posterior construct in the process. The same concept applies to independent posterior revisions. Other constructions for detachably securing the posterior part to the anterior part are possible.

Alternate embodiments may also exist whereby the method and system described are assembled in reverse order resulting in an anterior and posterior joined construct using the pedicle connectors described herein. Such an embodiment would require an initial posterior incision and pedicle connector and posterior stabilization construct prior to turning the patient over and completing the anterior construct assembly. This alternate technique may or may not involve guide wires.

It is to be understood that while the invention has been described in conjunction with the specific embodiments thereof, as well as the preceding examples, these embodiment and examples are intended merely to illustrate and not limit the scope of the invention. Other aspects, advantages and modifications within the scope of the invention will be apparent to those skilled in the art to which the invention pertains

I claim:

1. A method for stabilizing the spine at the level of one or more vertebrae having anterior and posterior sides, comprising the steps of:
    inserting a pedicle connector through the pedicle of a vertebra from one of the anterior side and the posterior side of a vertebra to the other of the anterior side and the posterior side of the vertebra, wherein the step of inserting a pedicle connector comprises the step of positioning a guide wire through the vertebra to guide the placement of the connector, wherein a needle is positioned through the vertebra, and the guide wire is directed through the needle and through the vertebra, and the needle is removed to leave the guide wire in position through the vertebra, wherein the anterior stabilization construct is threaded onto the wire to position the stabilization construct adjacent to the anterior surface of the vertebra;
    securing the pedicle connector to a stabilization construct positioned adjacent to either the anterior side of the pedicle connector or the posterior side of the pedicle connector;
    repeating the process for the opposite side of the pedicle connector.

2. A method for stabilizing the spine at the level of one or more vertebrae having anterior and posterior sides, comprising the steps of:
    inserting a pedicle connector through the pedicle of a vertebra from one of the anterior side and the posterior side of a vertebra to the other of the anterior side and the posterior side of the vertebra;
    securing the pedicle connector to a stabilization construct positioned adjacent to either the anterior side of the pedicle connector or the posterior side of the pedicle connector;
    repeating the process for the opposite side of the pedicle connector;
    wherein the pedicle connector is secured to the stabilization construct by locking screws.

3. The method of claim 2, wherein the stabilization construct is placed over the wire on the posterior side of the vertebra and attached to the pedicle connector.

4. The method of claim 3 wherein the pedicle connector is a screw.

* * * * *